(12) United States Patent
Barnes et al.

(10) Patent No.: US 6,518,399 B1
(45) Date of Patent: Feb. 11, 2003

(54) RECEPTOR

(75) Inventors: Ashley Antony Barnes, Herts (GB); Alan Wise, Bedfordshire (GB); Fiona Hamilton Marshall, Hertfordshire (GB); Neil James Fraser, Herts (GB); Julia Helen Margaret White, Herts (GB); Steven Michael Foord, Buckinghamshire (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/390,134

(22) Filed: Sep. 3, 1999

Related U.S. Application Data
(60) Provisional application No. 60/103,670, filed on Oct. 9, 1998.

(30) Foreign Application Priority Data

Sep. 7, 1998 (GB) .............................................. 9819420

(51) Int. Cl.[7] .......................... C07K 1/00; C07H 21/04; C12N 1/20; C12P 21/06; G01N 33/566
(52) U.S. Cl. .......................... 530/350; 435/6; 435/7.21; 435/69.1; 435/252.3; 435/320.1; 435/325; 514/2; 536/23.5; 436/501
(58) Field of Search ........................ 530/350; 536/23.5; 514/2; 435/6, 7.21, 325, 69.1, 282.3, 320.1; 436/501

(56) References Cited

U.S. PATENT DOCUMENTS
6,043,054 A * 3/2000 Vawter et al. ............. 435/69.1

FOREIGN PATENT DOCUMENTS

| | | |
|---|---|---|
| EP | 0 937 777 | 8/1999 |
| WO | 97/46675 | 12/1997 |
| WO | 99/20751 | 4/1999 |
| WO | WO 99/21890 | 5/1999 |
| WO | WO 99/51636 | 10/1999 |
| WO | WO 99/61606 | 12/1999 |

OTHER PUBLICATIONS

Kaupmann K. et al., Nature 386:239, Mar. 1997.*
Bowery TiPS 18(103), 1997.*
Kuner et al. Science 283(74–77), 1999.*
Hirouchi et al. Pharm. Rev. Commun. 8(151), 1996.*
Bowie et al., Science 247:1306–1310, 1990.*
Wells Biochemistry 29:8509–8517, 1990.*
Ngo et al. The Protein Folding Problem and Tertiary Structure, pp 492–495, 1994.*
Kaupmann, et al., "Expression Cloning of GABaB receptors uncovers similarity to metabotropic glumate receptors", Nature, vol. 386: 239–246, Mar. 20, 1997.

* cited by examiner

Primary Examiner—Yvonne Eyler
Assistant Examiner—Michael Brannock
(74) Attorney, Agent, or Firm—Michael M. Conger

(57) ABSTRACT

The present invention relates to the novel $GABA_B$ receptor subtypes $GABA_B$-R1c and $GABA_B$-R2 as well as to a novel, functional $GABA_B$ receptor which comprises a heterodimer of $GABA_B$-R1 and $GABA_B$-R2 receptor subunits. The present invention also relates to variants of the receptors, nucleotide sequences encoding the receptors and variants thereof and novel vectors, stable cell lines, antibodies, screening methods, methods of treatment and methods of receptor production.

3 Claims, 21 Drawing Sheets

Nucleotide Sequence

```
ATGGCTTCCCCGCGGAGCTCCGGGCAGCCCGGGCCGCCGCCGCCGCCGCCACCGCCGCCC       60
GCGCGCCTGCTACTGCTACTGCTGCTGCCGCTGCTGCTGCCTCTGGCGCCCGGGGCCTGG      120
GGCTGGGCGCGGGGCGCCCCCGGCCGCCGCCCAGCAGCCCGCCGCTCTCCATCATGGGC       180
CTCATGCCGCTCACCAAGGAGGTGGCCAAGGGCAGCATCGGGCGCGGTGTGCTCCCCGCC      240
GTGGAACTGGCCATCGAGCAGATCCGCAACGAGTCACTCCTGCGCCCCTACTTCCTCGAC      300
CTGCGGCTCTATGACACGGAGTGCGACAACGCAAAAGGGTTGAAAGCCTTCTACGATGCA      360
ATAAAATACGGGCCTAACCACTTGATGGTGTTTGGAGGCGTCTGTCCATCCGTCACATCC      420
ATCATTGCAGAGTCCCTCCAAGGCTGGAATCTGGTGCAGCTTTCTTTTGCTGCAACCACG      480
CCTGTTCTAGCCGATAAGAAAAAATACCCTTATTTCTTTCGGACCGTCCCATCAGACAAT      540
GCGGTGAATCCAGCCATTCTGAAGTTGCTCAAGCACTACCAGTGGAAGCGCGTGGGCACG      600
CTGACGCAAGACGTTCAGAGGTTCTCTGAGGTGCGGAATGACCTGACTGGAGTTCTGTAT      660
GGCGAGGACATTGAGATTTCAGACACCGAGAGCTTCTCCAACGATCCCTGTACCAGTGTC      720
AAAAAGCTGAAGGGGAATGATGTGCGGATCATCCTTGGCCAGTTTGACCAGAATATGGCA      780
GCAAAAGTGTTCTGTTGTGCATACGAGGAGAACATGTATGGTAGTAAATATCAGTGGATC      840
ATTCCGGGCTGGTACGAGCCTTCTTGGTGGGAGCAGGTGCACACGGAAGCCAACTCATCC      900
CGCTGCCTCCGGAAGAATCTGCTTGCTGCCATGGAGGGCTACATTGGCGTGGATTTCGAG      960
CCCCTGAGCTCCAAGCAGATCAAGACCATCTCAGGAAAGACTCCACAGCAGTATGAGAGA     1020
GAGTACAACAACAAGCGGTCAGGCGTGGGGCCCAGCAAGTTCCACGGGTACGCCTACGAT     1080
GGCATCTGGGTCATCGCCAAGACACTGCAGAGGGCCATGGAGACACTGCATGCCAGCAGC     1140
CGGCACCAGCGGATCCAGGACTTCAACTACACGGACCACACGCTGGGCAGGATCATCCTC     1200
AATGCCATGAACGAGACCAACTTCTTCGGGGTCACGGGTCAAGTTGTATTCCGGAATGGG     1260
GAGAGAATGGGGACCATTAAATTTACTCAATTTCAAGACAGCAGGGAGGTGAAGGTGGGA     1320
GAGTACAACGCTGTGGCCGACACACTGGAGATCATCAATGACACCATCAGGTTCCAAGGA     1380
TCCGAACCACCAAAAGACAAGACCATCATCCTGGAGCAGCTGCGGAAGATCTCCCTACCT     1440
CTCTACAGCATCCTCTCTGCCCTCACCATCCTCGGGATGATCATGGCCAGTGCTTTTCTC     1500
TTCTTCAACATCAAGAACCGGAATCAGAAGCTCATAAAGATGTCGAGTCCATACATGAAC     1560
AACCTTATCATCCTTGGAGGGATGCTCTCCTATGCTTCCATATTTCTCTTTGGCCTTGAT     1620
GGATCCTTTGTCTCTGAAAAGACCTTTGAAACACTTTGCACCGTCAGGACCTGGATTCTC     1680
ACCGTGGGCTACACGACCGCTTTTGGGGCCATGTTTGCAAAGACCTGGAGAGTCCACGCC     1740
ATCTTCAAAAATGTGAAAATGAAGAAGAAGATCATCAAGGACCAGAAACTGCTTGTGATC     1800
GTGGGGGGCATGCTGCTGATCGACCTGTGTATCCTGATCTGCTGGCAGGCTGTGGACCCC     1860
```

FIGURE 1A-1

```
CTGCGAAGGACAGTGGAGAAGTACAGCATGGAGCCGGACCCAGCAGGACGGGATATCTCC    1920
ATCCGCCCTCTCCTGGAGCACTGTGAGAACACCCATATGACCATCTGGCTTGGCATCGTC    1980
TATGCCTACAAGGGACTTCTCATGTTGTTCGGTTGTTTCTTAGCTTGGGAGACCCGCAAC    2040
GTCAGCATCCCCGCACTCAACGACAGCAAGTACATCGGGATGAGTGTCTACAACGTGGGG    2100
ATCATGTGCATCATCGGGGCCGCTGTCTCCTTCCTGACCCGGGACCAGCCCAATGTGCAG    2160
TTCTGCATCGTGGCTCTGGTCATCATCTTCTGCAGCACCATCACCCTCTGCCTGGTATTC    2220
GTGCCGAAGCTCATCACCCTGAGAACAAACCCAGATGCAGCAACGCAGAACAGGCGATTC    2280
CAGTTCACTCAGAATCAGAAGAAAGAAGATTCTAAAACGTCCACCTCGGTCACCAGTGTG    2340
AACCAAGCCAGCACATCCCGCCTGGAGGGCCTACAGTCAGAAAACCATCGCCTGCGAATG    2400
AAGATCACAGAGCTGGATAAAGACTTGGAAGAGGTCACCATGCAGCTGCAGGACACACCA    2460
GAAAAGACCACCTACATTAAACAGAACCACTACCAAGAGCTCAATGACATCCTCAACCTG    2520
GGAAACTTCACTGAGAGCACAGATGGAGGAAAGGCCATTTTAAAAAATCACCTCGATCAA    2580
AATCCCCAGCTACAGTGGAACACAACAGAGCCCTCTCGAACATGCAAAGATCCTATAGAA    2640
GATATAAACTCTCCAGAACACATCCAGCGTCGGCTGTCCCTCCAGCTCCCCATCCTCCAC    2700
CACGCCTACCTCCCATCCATCGGAGGCGTGGACGCCAGCTGTGTCAGCCCCTGCGTCAGC    2760
CCCACCGCCAGCCCCCGCCACAGACATGTGCCACCCTCCTTCCGAGTCATGGTCTCGGGC    2820
CTGTAA
```

FIGURE 1A-2

Protein Sequence

```
MASPRSSGQPGPPPPPPPPPARLLLLLLLPLLLPLAPGAWGWARGAPRPPPSSPPLSIMG    60
LMPLTKEVAKGSIGRGVLPAVELAIEQIRNESLLRPYFLDLRLYDTECDNAKGLKAFYDA   120
IKYGPNHLMVFGGVCPSVTSIIAESLQGWNLVQLSFAATTPVLADKKKYPYFFRTVPSDN   180
AVNPAILKLLKHYQWKRVGTLTQDVQRFSEVRNDLTGVLYGEDIEISDTESFSNDPCTSV   240
KKLKGNDVRIILGQFDQNMAAKVFCCAYEENMYGSKYQWIIPGWYEPSWWEQVHTEANSS   300
RCLRKNLLAAMEGYIGVDFEPLSSKQIKTISGKTPQQYEREYNNKRSGVGPSKFHGYAYD   360
GIWVIAKTLQRAMETLHASSRHQRIQDFNYTDHTLGRIILNAMNETNFFGVTGQVVFRNG   420
ERMGTIKFTQFQDSREVKVGEYNAVADTLEIINDTIRFQGSEPPKDKTIILEQLRKISLP   480
LYSILSALTILGMIMASAFLFFNIKNRNQKLIKMSSPYMNNLIILGGMLSYASIFLFGLD   540
GSFVSEKTFETLCTVRTWILTVGYTTAFGAMFAKTWRVHAIFKNVKMKKKIIKDQKLLVI   600
VGGMLLIDLCILICWQAVDPLRRTVEKYSMEPDPAGRDISIRPLLEHCENTHMTIWLGIV   660
YAYKGLLMLFGCFLAWETRNVSIPALNDSKYIGMSVYNVGIMCIIGAAVSFLTRDQPNVQ   720
FCIVALVIIFCSTITLCLVFVPKLITLRTNPDAATQNRRFQFTQNQKKEDSKTSTSVTSV   780
NQASTSRLEGLQSENHRLRMKITELDKDLEEVTMQLQDTPEKTTYIKQNHYQELNDILNL   840
GNFTESTDGGKAILKNHLDQNPQLQWNTTEPSRTCKDPIEDINSPEHIQRRLSLQLPILH   900
HAYLPSIGGVDASCVSPCVSPTASPRHRHVPPSFRVMVSGL                      941
```

FIGURE 1B

```
GABAb1a              MLLLLLAPLFLRPPGA .............
GGAQTPNATSEGCQIIHPPWEGGIRYRGLTRDQVKAINFLPVDYEIEYVCRGEREV  (SEQIDNO: 32)
GABAb1b              MGPGAPFARVGWPLPLLVVMAAGVAPVWA .............  (SEQIDNO: 33)
GAGAb2      MASPRSSGQPGPPPPPPPPPARLLLLLLLPLLLPLAPG .............  (SEQIDNO: 34)

GABAb1a
VGPKVRKCLANGSWTDMDTPSRCVRICSKSYLTLENGKVFLTGGDLPALDGARVDFRCDPDF
HLVGSSRSICSQGQWSTPKPHCQVNRTPH  (SEQIDNO: 35)
GABAb1a/b
                    SERRAVYIG  (SEQIDNO: 36)
GABAb1b
     SHSPHLPRPHSRVPPHPS  (SEQIDNO: 37)
GABAb2
       AWGWARGAPRPPPSSPPLS...IMGLM  (SEQIDNO: 38)

GABAb1
ALFPMSGGWPGGQACQPAVEMALEDVNSRRDILPDYELKLIHHDSKCDPGQATKYLYELLYN
DPIKIILMPG.CSSVSTLVAEAARMWNLIVLSYGSSSPA  (SEQIDNO: 39)
GABAb2
PLTKEVAKGSIGRGVLPAVELAIEQIRN.ESLLRPYFLDLRLYDTECDNAKGLKAFYDAIKY
GPNHLMVFGGVCPSVTSIIAESLQGWNLVQLSFAATTPV  (SEQIDNO: 40)
                    *

GABAb1
LSNRQRFPTFFRTHPSATLHNPTRVKLFEKWGWKKIATIQQTTEVFTSTLDDLEERVKEAGI
EITFRQSFFSDPAVPVKNLKRQDARIIVGLFYETEARKV  (SEQIDNO: 41)
GABAb2
LADKKKYPYFFRTVPSDNAVNPAILKLLKHYQWKRVGTLTQDVQRFSEVRNDLTGVLYGEDI
EISDTESFSNDPCTSVKKLKGNDVRIILGQFDQNMAAKV  (SEQIDNO: 42)
```

FIGURE 2A

GABAb1
FCEVYKERLFGKKYVWFLIGWYADNWFKIYDPSIN...CTVDEMTEAVEGHITTEIVMLNPA
NTRSISNMTSQEFV.EKLTKRLKRHPEETGGFQEAPLAY (SEQIDNO: 43)
GABAb2
FCCAYEENMYGSKYQWIIPGWYEPSWWEQVHTEANSSRCLRKNLLAAMEGYIGVDFEPLSSK
QIKTISGKTPQQYEREYNNKRSGVGPSKFHGY.....AY (SEQIDNO: 44)
                                  *
GABAb1
DAIWALALALNKTSGGGGRSG..VRLEDFNYNNQTITDQIYRAMNSSSFEGVSGHVVFDASG
SRMAWTLIEQPQGGSYKKIGYYDSTKDDLS.WSKTDKWIG (SEQIDNO: 45)
GABAb2
DGIWVIAKTLQRAMETLHASSRHQRIQDFNYTDHTLGRIILNAMNETNFFGVTGQVVF.RNG
ERMG.TIKFTQFQDSREVKVGEYNAVADTLEIINDTIRFQ (SEQIDNO: 46)
                                *         *
                *
GABAb1
GSPPA.DQTLVIKTFRFLSQKLFISVSVLSSLGIVLAVVCLSFNIYNSHVRYIQNSQPNLNN
LTAVGCSLALAAVFPLGLDGYHIGRNQFPFVCQARLWLLG (SEQIDNO: 47)
GABAb2
GSEPPKDKTIILEQLRKISLPLYSILSALTILGMIMASAFLFFNIKNRNQKLIKMSSPYMNN
LIILGGMLSYASIFLFGLDGSFVSEKTFETLCTVRTWILT (SEQIDNO: 48)
                                        TMI
TMII
GABAb1
LGFSLGYGSMFTKIWWVHTGFTKKEEKKEWRKTLEPWKLYATVGLLVGMDVLTLAIWQIVDP
LHRTIETFAKEEPKEDIDVSILPQLEHCSSRKMNTWLGIF (SEQIDNO: 49)
GABAb2
VGYTTAFGAMFAKTWRVHAIFKNVKMKKKIIKDQK...LLVIVGGMLLIDLCILICWQAVDP
LRRTVEKYSMEPDPAGRDISIRPLLEHCENTHMTIWLGIV (SEQIDNO: 50)
        TMIII                          TMIV

FIGURE 2B

BAIT→
GABAb1
YGYKGLLLLLGIFLAYETKSVSTEKINDHRAVGMAIYNVAVLCLITAPVTMILSSQQDAAFA
FASLAIVFSSYITLVVLFVPKMRRLITRGE..........(SEQIDNO: 51)
GABAb2
YAYKGLLMLFGCFLAWETRNVSIPALNDSKYIGMSVYNVGIMCIIGAAVSFLTRDQPNVQFC
IVALVIIFCSTITLCLVFVPK...LITLRTNPDAATQNRR (SEQIDNO: 52)
        TMV                      TMVI
  TMVII

GABAb1
WQSEA.QDTMKTGSSTNNNEEEK...SRLLEK..ENRELEKIIAEKEERVSELRHQLQSRQQ
LRSRRHPPTPPEPSGGLPRGPPEPPDRLSCDGSRVHLLYK (SEQIDNO: 53)
GABAb2
FQFTQNQKKEDSKTSTSVTSVNQASTSRLEGLQSENHRLRMKITELDKDLEEVTMQLQDTPE
KTTYIKQNHYQELNDILNLGNFTESTDGGKAILKNHLDQN (SEQIDNO: 54)
       Y2H HITS→

GABAb2
PQLQWNTTEPSRTCKDPIEDINSPEHIQRRLSLQLPILHHAYLPSIGGVDASCVSPCVSPTA
SPRHRHVPPSFRVMVSGL (SEQIDNO: 55)

FIGURE 2C

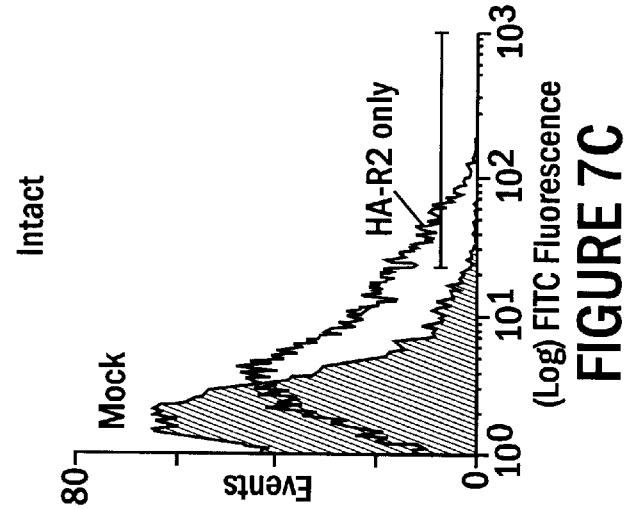
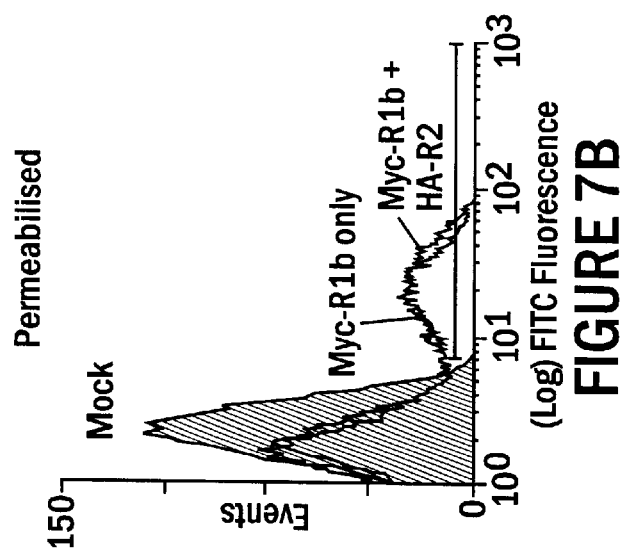
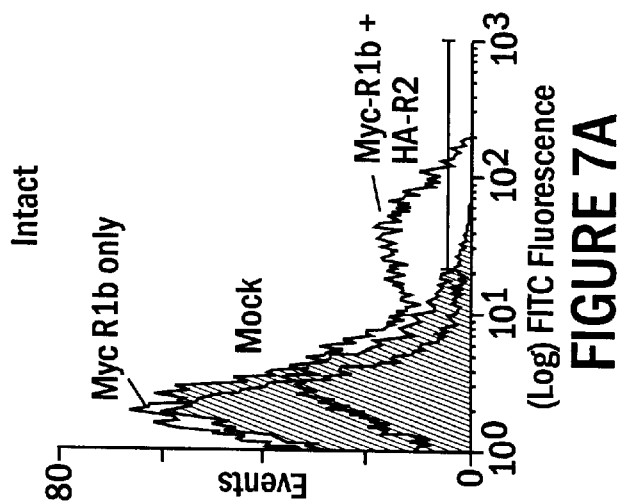

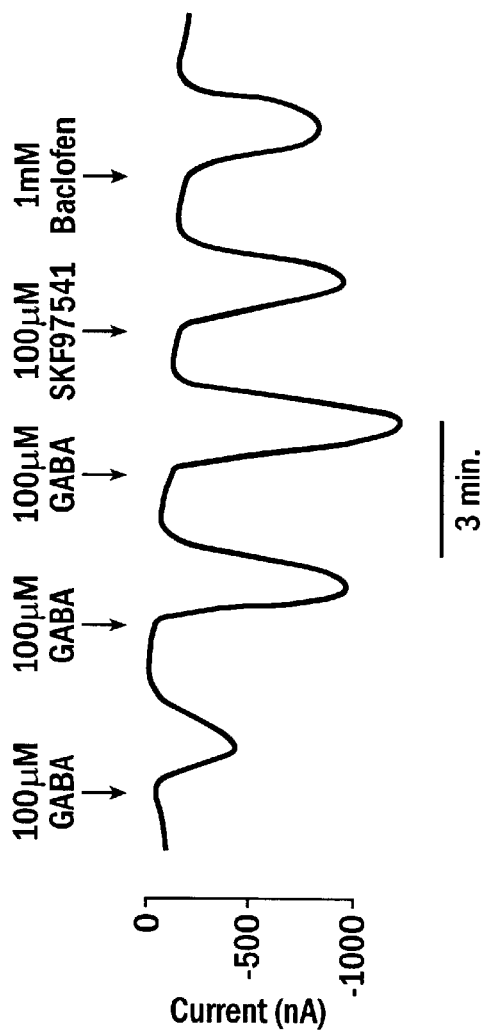
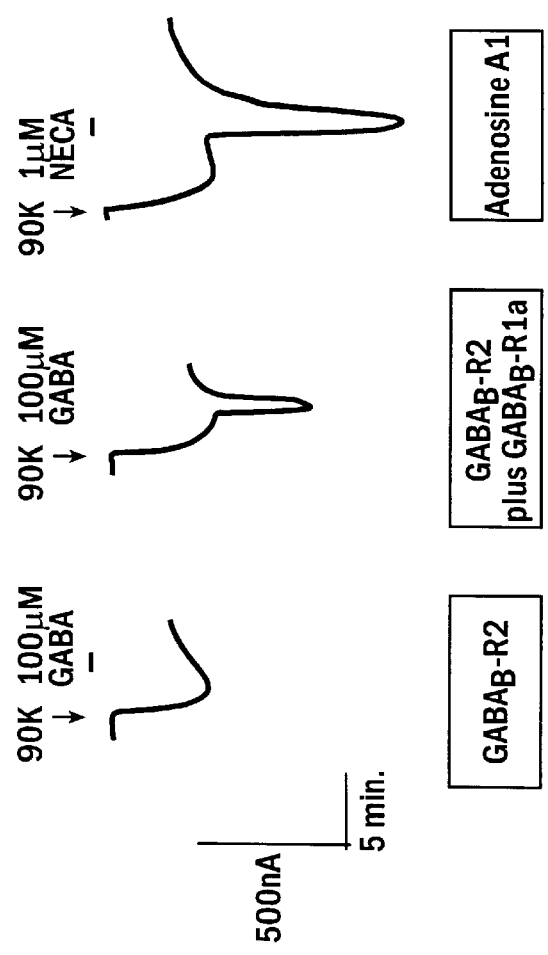
FIGURE 12A
FIGURE 12B

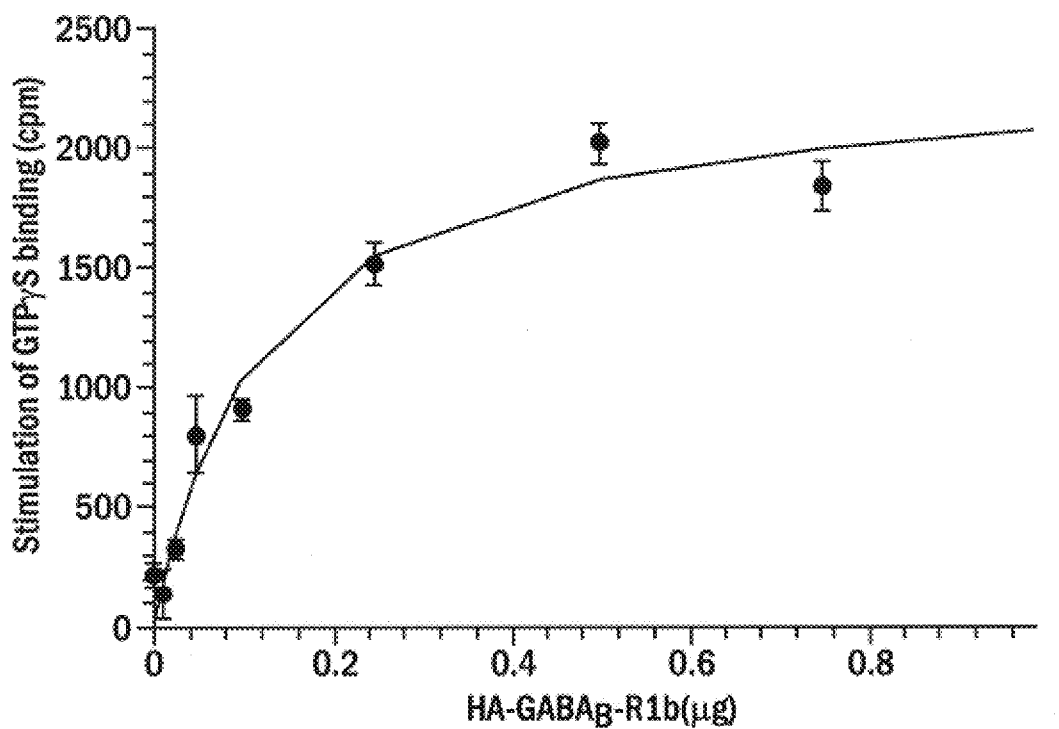
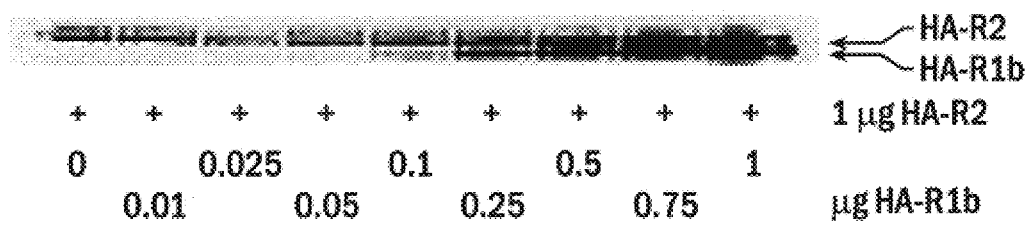
FIGURE 14

SEQUENCE LISTING

```
<160> NUMBER OF SEQ ID NOS: 55

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gcgactgctg tgggctgctt actggc                                        26

<210> SEQ ID NO 2
<211> LENGTH: 30
<212> TYPE: DNA
<213> ORGANISM: Artificial Sequence
<220> FEATURE:
<223> OTHER INFORMATION: primer
```

-continued

```
<400> SEQUENCE: 2
gcgaattccc tgtcctccct caccctaccc                                    30

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ccgagctcaa gctcatccac cacg                                          24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tcttcctcca ctccttcttt tctt                                          24

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
tgagctggag ccataggaaa gcacaat                                       27

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
gatcttgata gggtcgttgt agagca                                        26

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gctcctaacg ctccccaaca                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggcctggatc acacttgctg                                               20

<210> SEQ ID NO 9
<211> LENGTH: 19
```

```
<212> TYPE: DNA
<213> ORGANISM: Artificial Sequence
<220> FEATURE:
<223> OTHER INFORMATION: primer

<400> SEQUENCE: 9
cccaacgcca cctcagaag                                               19

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
ccgctcatgg gaaacagtg                                               19

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
ccccggcaca catactcaat ctcatag                                      27

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ccggtacctg atgccccctt cc                                           22

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
cgagatgttg ctgctgctgc ta                                           22

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
taggatccca ctcccccat ccc                                           23

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
```

-continued

```
ccagcgtgga gacagagctg                                               20

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
atggcttccc cgcggag                                                  17

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
gaacaggcgt ggttgcag                                                 18

<210> SEQ ID NO 18
<211> LENGTH: 48
<212> TYPE: DNA
<213> ORGANISM: Artificial Sequence
<220> FEATURE:
<223> OTHER INFORMATION: constructed oligo

<400> SEQUENCE: 18
agcttctcga ggcttgggga tgggcacgag gagctcctgc tcggccgg                48

<210> SEQ ID NO 19
<211> LENGTH: 48
<212> TYPE: DNA
<213> ORGANISM: Artificial Sequence
<220> FEATURE:
<223> OTHER INFORMATION: constructed oligo

<400> SEQUENCE: 19
agagctccga acccctaccc gtgctcctcg tggtcgagcc ggccttaa                48

<210> SEQ ID NO 20
<211> LENGTH: 10
<212> TYPE: PRT
<213> ORGANISM: Artificial Sequence
<220> FEATURE:
<223> OTHER INFORMATION: synthetic peptide

<400> SEQUENCE: 20

Ala Trp Gly Trp Ala Arg Gly Ala Pro Arg
 1               5                  10

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
cgcctggagg acttcaacta caa                                           23

<210> SEQ ID NO 22
<211> LENGTH: 23
<212> TYPE: DNA
```

```
<213> ORGANISM: Artificial Sequence
<220> FEATURE:
<223> OTHER INFORMATION: primer

<400> SEQUENCE: 22
tcctcccaat gtggtaacca tcg                                              23

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
acaagaccat catcctgga                                                   19

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gatcacaagc agtttctggt c                                                21

<210> SEQ ID NO 25
<211> LENGTH: 39
<212> TYPE: DNA
<213> ORGANISM: Artificial Sequence
<220> FEATURE:
<223> OTHER INFORMATION: primer

<400> SEQUENCE: 25
gttgtcccca tggtgcccaa gatgcgcagg ctgatcacc                             39

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
gtcctgcggc cgcggatcct cacttataaa gcaaatgcac tcg                        43

<210> SEQ ID NO 27
<211> LENGTH: 47
<212> TYPE: DNA
<213> ORGANISM: Artificial Sequence
<220> FEATURE:
<223> OTHER INFORMATION: primer

<400> SEQUENCE: 27
ctctgcccca tggccgtgcc gaagctcatc accctgagaa caaaccc                    47

<210> SEQ ID NO 28
<211> LENGTH: 51
<212> TYPE: DNA
<213> ORGANISM: Artificial Sequence
<220> FEATURE:
<223> OTHER INFORMATION: primer

<400> SEQUENCE: 28
ggcccagggc ggccgcactt acaggcccga gaccatgact cggaaggagg g               51
```

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
cagggatgtt taataccact acaatgg                                              27

<210> SEQ ID NO 30
<211> LENGTH: 2826
<212> TYPE: DNA
<213> ORGANISM: Homo sapiens

<400> SEQUENCE: 30

| | | | | | |
|---|---|---|---|---|---|
| atggcttccc | cgcggagctc | cgggcagccc | gggccgccgc | cgccgccgcc | accgccgccc      60 |
| gcgcgcctgc | tactgctact | gctgctgccg | ctgctgctgc | ctctggcgcc | cggggcctgg     120 |
| ggctgggcgc | gggcgccccc | ccggccgccg | cccagcagcc | cgccgctctc | catcatgggc     180 |
| ctcatgccgc | tcaccaagga | ggtggccaag | gcagcatcg  | ggcgcggtgt | gctccccgcc     240 |
| gtggaactgg | ccatcgagca | gatccgcaac | gagtcactcc | tgcgcccta  | cttcctcgac     300 |
| ctgcggctct | atgacacgga | gtgcgacaac | gcaaaaggt  | tgaaagcctt | ctacgatgca     360 |
| ataaaatacg | gcctaacca  | cttgatggtg | tttggaggcg | tctgtccatc | cgtcacatcc     420 |
| atcattgcag | agtccctcca | aggctggaat | ctggtgcagc | tttcttttgc | tgcaaccacg     480 |
| cctgttctag | ccgataagaa | aaataccct  | tatttctttc | ggaccgtccc | atcagacaat     540 |
| gcggtgaatc | cagccattct | gaagttgctc | aagcactacc | agtggaagcg | cgtgggcacg     600 |
| ctgacgcaag | acgttcagag | gttctctgag | gtgcggaatg | acctgactgg | agttctgtat     660 |
| ggcgaggaca | ttgagattc  | agacaccgag | agcttctcca | acgatccctg | taccagtgtc     720 |
| aaaaagctga | aggggaatga | tgtgcggatc | atccttggcc | agtttgacca | gaatatggca     780 |
| gcaaaagtgt | tctgttgtgc | atacgaggag | aacatgtatg | gtagtaaata | tcagtggatc     840 |
| attccgggct | ggtacgagcc | ttcttggtgg | gagcaggtgc | cacggaagc  | caactcatcc     900 |
| cgctgcctcc | ggaagaatct | gcttgctgcc | atggagggct | acattggcgt | ggatttcgag     960 |
| cccctgagct | ccaagcagat | caagaccatc | tcaggaaaga | ctccacagca | gtatgagaga    1020 |
| gagtacaaca | acaagcggtc | aggcgtgggg | cccagcaagt | tccacgggta | cgcctacgat    1080 |
| ggcatctggg | tcatcgccaa | gactctgcag | agggccatgg | agacactgca | tgccagcagc    1140 |
| cggcaccagc | ggatccagga | cttcaactac | acggaccaca | cgctgggcag | gatcatcctc    1200 |
| aatgccatga | acgagaccaa | cttcttcggg | gtcacgggtc | aagttgtatt | ccggaatggg    1260 |
| gagagaatgg | ggaccattaa | atttactcaa | tttcaagaca | gcagggaggt | gaaggtggga    1320 |
| gagtacaacg | ctgtggccga | cactggag  | atcatcaatg | acaccatcag | gttccaagga    1380 |
| tccgaaccac | caaaagacaa | gaccatcatc | ctggagcagc | tgcggaagat | ctccctacct    1440 |
| ctctacagca | tcctctctgc | cctcaccatc | ctcgggatga | tcatggccag | tgcttttctc    1500 |
| ttcttcaaca | tcaagaaccg | gaatcagaag | ctcataaaga | tgtcgagtcc | atacatgaac    1560 |
| aaccttatca | tccttggagg | gatgctctcc | tatgcttcca | tatttctctt | ggccttgat    1620 |
| ggatcctttg | tctctgaaaa | gacctttgaa | acacttgca  | ccgtcaggac | ctggattctc    1680 |
| accgtgggct | acacgaccgc | ttttgggcc  | atgtttgcaa | agacctggag | agtccacgcc    1740 |

-continued

```
atcttcaaaa atgtgaaaat gaagaagaag atcatcaagg accagaaact gcttgtgatc    1800 gtgggggca tgctgctgat cgacctgtgt atcctgatct gctggcaggc tgtggacccc    1860
ctgcgaagga cagtggagaa gtacagcatg gagccggacc cagcaggacg ggatatctcc    1920
atccgccctc tcctggagca ctgtgagaac acccatatga ccatctggct tggcatcgtc    1980
tatgcctaca agggacttct catgttgttc ggttgtttct tagcttggga gacccgcaac    2040
gtcagcatcc ccgcactcaa cgacagcaag tacatcggga tgagtgtcta caacgtgggg    2100
atcatgtgca tcatcggggc cgctgtctcc ttcctgaccc gggaccagcc caatgtgcag    2160
ttctgcatcg tggctctggt catcatcttc tgcagcacca tcaccctctg cctggtattc    2220
gtgccgaagc tcatcaccct gagaacaaac ccagatgcag caacgcagaa caggcgattc    2280
cagttcactc agaatcagaa gaaagaagat tctaaaacgt ccacctcggt caccagtgtg    2340
aaccaagcca gcacatcccg cctggagggc ctacagtcag aaaaccatcg cctgcgaatg    2400
aagatcacag agctggataa agacttggaa gaggtcacca tgcagctgca ggacacacca    2460
gaaaagacca cctacattaa acagaaccac taccaagagc tcaatgacat cctcaacctg    2520
ggaaacttca ctgagagcac agatggagga aaggccattt taaaaaatca cctcgatcaa    2580
aatccccagc tacagtggaa cacaacagag ccctctcgaa catgcaaaga tcctatagaa    2640
gatataaact ctccagaaca catccagcgt cggctgtccc tccagctccc catcctccac    2700
cacgcctacc tccatccat cggaggcgtg gacgccagct gtgtcagccc tgcgtcagc    2760 cccaccgcca gccccccgcca cagacatgtg ccaccctcct ccgagtcat ggtctcgggc    2820 ctgtaa                                                                2826
```

<210> SEQ ID NO 31
<211> LENGTH: 941
<212> TYPE: PRT
<213> ORGANISM: Homo sapiens

<400> SEQUENCE: 31

```
Met Ala Ser Pro Arg Ser Ser Gly Gln Pro Gly Pro Pro Pro Pro Pro
 1               5                  10                  15

Pro Pro Pro Pro Ala Arg Leu Leu Leu Leu Leu Leu Pro Leu Leu
                20                  25                  30

Leu Pro Leu Ala Pro Gly Ala Trp Gly Trp Ala Arg Gly Ala Pro Arg
         35                  40                  45

Pro Pro Pro Ser Ser Pro Pro Leu Ser Ile Met Gly Leu Met Pro Leu
     50                  55                  60

Thr Lys Glu Val Ala Lys Gly Ser Ile Gly Arg Gly Val Leu Pro Ala
 65                  70                  75                  80

Val Glu Leu Ala Ile Glu Gln Ile Arg Asn Glu Ser Leu Leu Arg Pro
                 85                  90                  95

Tyr Phe Leu Asp Leu Arg Leu Tyr Asp Thr Glu Cys Asp Asn Ala Lys
                100                 105                 110

Gly Leu Lys Ala Phe Tyr Asp Ala Ile Lys Tyr Gly Pro Asn His Leu
            115                 120                 125

Met Val Phe Gly Gly Val Cys Pro Ser Val Thr Ser Ile Ile Ala Glu
        130                 135                 140

Ser Leu Gln Gly Trp Asn Leu Val Gln Leu Ser Phe Ala Ala Thr Thr
145                 150                 155                 160

Pro Val Leu Ala Asp Lys Lys Tyr Pro Tyr Phe Phe Arg Thr Val
                165                 170                 175
```

-continued

Pro Ser Asp Asn Ala Val Asn Pro Ala Ile Leu Lys Leu Leu Lys His
            180                 185                 190

Tyr Gln Trp Lys Arg Val Gly Thr Leu Thr Gln Asp Val Gln Arg Phe
        195                 200                 205

Ser Glu Val Arg Asn Asp Leu Thr Gly Val Leu Tyr Gly Glu Asp Ile
        210                 215                 220

Glu Ile Ser Asp Thr Glu Ser Phe Ser Asn Asp Pro Cys Thr Ser Val
225                 230                 235                 240

Lys Lys Leu Lys Gly Asn Asp Val Arg Ile Ile Leu Gly Gln Phe Asp
                245                 250                 255

Gln Asn Met Ala Ala Lys Val Phe Cys Cys Ala Tyr Glu Glu Asn Met
            260                 265                 270

Tyr Gly Ser Lys Tyr Gln Trp Ile Ile Pro Gly Trp Tyr Glu Pro Ser
        275                 280                 285

Trp Trp Glu Gln Val His Thr Glu Ala Asn Ser Ser Arg Cys Leu Arg
        290                 295                 300

Lys Asn Leu Leu Ala Ala Met Glu Gly Tyr Ile Gly Val Asp Phe Glu
305                 310                 315                 320

Pro Leu Ser Ser Lys Gln Ile Lys Thr Ile Ser Gly Lys Thr Pro Gln
                325                 330                 335

Gln Tyr Glu Arg Glu Tyr Asn Asn Lys Arg Ser Gly Val Gly Pro Ser
            340                 345                 350

Lys Phe His Gly Tyr Ala Tyr Asp Gly Ile Trp Val Ile Ala Lys Thr
        355                 360                 365

Leu Gln Arg Ala Met Glu Thr Leu His Ala Ser Ser Arg His Gln Arg
        370                 375                 380

Ile Gln Asp Phe Asn Tyr Thr Asp His Thr Leu Gly Arg Ile Ile Leu
385                 390                 395                 400

Asn Ala Met Asn Glu Thr Asn Phe Phe Gly Val Thr Gly Gln Val Val
                405                 410                 415

Phe Arg Asn Gly Glu Arg Met Gly Thr Ile Lys Phe Thr Gln Phe Gln
            420                 425                 430

Asp Ser Arg Glu Val Lys Val Gly Glu Tyr Asn Ala Val Ala Asp Thr
        435                 440                 445

Leu Glu Ile Ile Asn Asp Thr Ile Arg Phe Gln Gly Ser Glu Pro Pro
        450                 455                 460

Lys Asp Lys Thr Ile Ile Leu Glu Gln Leu Arg Lys Ile Ser Leu Pro
465                 470                 475                 480

Leu Tyr Ser Ile Leu Ser Ala Leu Thr Ile Leu Gly Met Ile Met Ala
                485                 490                 495

Ser Ala Phe Leu Phe Asn Ile Lys Asn Arg Asn Gln Lys Leu Ile
            500                 505                 510

Lys Met Ser Ser Pro Tyr Met Asn Asn Leu Ile Ile Leu Gly Gly Met
        515                 520                 525

Leu Ser Tyr Ala Ser Ile Phe Leu Phe Gly Leu Asp Gly Ser Phe Val
        530                 535                 540

Ser Glu Lys Thr Phe Glu Thr Leu Cys Thr Val Arg Thr Trp Ile Leu
545                 550                 555                 560

Thr Val Gly Tyr Thr Thr Ala Phe Gly Ala Met Phe Ala Lys Thr Trp
                565                 570                 575

Arg Val His Ala Ile Phe Lys Asn Val Lys Met Lys Lys Lys Ile Ile
            580                 585                 590

Lys Asp Gln Lys Leu Leu Val Ile Val Gly Gly Met Leu Leu Ile Asp 595                 600                 605
Leu Cys Ile Leu Ile Cys Trp Gln Ala Val Asp Pro Leu Arg Arg Thr
610                 615                 620

Val Glu Lys Tyr Ser Met Glu Pro Asp Pro Ala Gly Arg Asp Ile Ser
625                 630                 635                 640

Ile Arg Pro Leu Leu Glu His Cys Glu Asn Thr His Met Thr Ile Trp
                645                 650                 655

Leu Gly Ile Val Tyr Ala Tyr Lys Gly Leu Leu Met Leu Phe Gly Cys
                660                 665                 670

Phe Leu Ala Trp Glu Thr Arg Asn Val Ser Ile Pro Ala Leu Asn Asp
                675                 680                 685

Ser Lys Tyr Ile Gly Met Ser Val Tyr Asn Val Gly Ile Met Cys Ile
        690                 695                 700

Ile Gly Ala Ala Val Ser Phe Leu Thr Arg Asp Gln Pro Asn Val Gln
705                 710                 715                 720

Phe Cys Ile Val Ala Leu Val Ile Ile Phe Cys Ser Thr Ile Thr Leu
                725                 730                 735

Cys Leu Val Phe Val Pro Lys Leu Ile Thr Leu Arg Thr Asn Pro Asp
                740                 745                 750

Ala Ala Thr Gln Asn Arg Arg Phe Gln Phe Thr Gln Asn Gln Lys Lys
                755                 760                 765

Glu Asp Ser Lys Thr Ser Thr Ser Val Thr Ser Val Asn Gln Ala Ser
770                 775                 780

Thr Ser Arg Leu Glu Gly Leu Gln Ser Glu Asn His Arg Leu Arg Met
785                 790                 795                 800

Lys Ile Thr Glu Leu Asp Lys Asp Leu Glu Glu Val Thr Met Gln Leu
                805                 810                 815

Gln Asp Thr Pro Glu Lys Thr Thr Tyr Ile Lys Gln Asn His Tyr Gln
                820                 825                 830

Glu Leu Asn Asp Ile Leu Asn Leu Gly Asn Phe Thr Glu Ser Thr Asp
                835                 840                 845

Gly Gly Lys Ala Ile Leu Lys Asn His Leu Asp Gln Asn Pro Gln Leu
        850                 855                 860

Gln Trp Asn Thr Thr Glu Pro Ser Arg Thr Cys Lys Asp Pro Ile Glu
865                 870                 875                 880

Asp Ile Asn Ser Pro Glu His Ile Gln Arg Arg Leu Ser Leu Gln Leu
                885                 890                 895

Pro Ile Leu His His Ala Tyr Leu Pro Ser Ile Gly Gly Val Asp Ala
                900                 905                 910

Ser Cys Val Ser Pro Cys Val Ser Pro Thr Ala Ser Pro Arg His Arg
        915                 920                 925

His Val Pro Pro Ser Phe Arg Val Met Val Ser Gly Leu
        930                 935                 940

<210> SEQ ID NO 32
<211> LENGTH: 72
<212> TYPE: PRT
<213> ORGANISM: Homo sapiens

<400> SEQUENCE: 32

Met Leu Leu Leu Leu Leu Ala Pro Leu Phe Leu Arg Pro Pro Gly Ala
1               5                   10                  15

Gly Gly Ala Gln Thr Pro Asn Ala Thr Ser Glu Gly Cys Gln Ile Ile
            20                  25                  30

-continued

His Pro Pro Trp Glu Gly Gly Ile Arg Tyr Arg Gly Leu Thr Arg Asp
            35                  40                  45

Gln Val Lys Ala Ile Asn Phe Leu Pro Val Asp Tyr Glu Ile Glu Tyr
        50                  55                  60

Val Cys Arg Gly Glu Arg Glu Val
65                  70

<210> SEQ ID NO 33
<211> LENGTH: 29
<212> TYPE: PRT
<213> ORGANISM: Homo sapiens

<400> SEQUENCE: 33

Met Gly Pro Gly Ala Pro Phe Ala Arg Val Gly Trp Pro Leu Pro Leu
1               5                   10                  15

Leu Val Val Met Ala Ala Gly Val Ala Pro Val Trp Ala
            20                  25

<210> SEQ ID NO 34
<211> LENGTH: 38
<212> TYPE: PRT
<213> ORGANISM: Homo sapiens

<400> SEQUENCE: 34

Met Ala Ser Pro Arg Ser Ser Gly Gln Pro Gly Pro Pro Pro Pro Pro
1               5                   10                  15

Pro Pro Pro Pro Ala Arg Leu Leu Leu Leu Leu Leu Leu Pro Leu Leu
            20                  25                  30

Leu Pro Leu Ala Pro Gly
            35

<210> SEQ ID NO 35
<211> LENGTH: 91
<212> TYPE: PRT
<213> ORGANISM: Homo sapiens

<400> SEQUENCE: 35

Val Gly Pro Lys Val Arg Lys Cys Leu Ala Asn Gly Ser Trp Thr Asp
1               5                   10                  15

Met Asp Thr Pro Ser Arg Cys Val Arg Ile Cys Ser Lys Ser Tyr Leu
            20                  25                  30

Thr Leu Glu Asn Gly Lys Val Phe Leu Thr Gly Gly Asp Leu Pro Ala
            35                  40                  45

Leu Asp Gly Ala Arg Val Asp Phe Arg Cys Asp Pro Asp Phe His Leu
        50                  55                  60

Val Gly Ser Ser Arg Ser Ile Cys Ser Gln Gly Gln Trp Ser Thr Pro
65                  70                  75                  80

Lys Pro His Cys Gln Val Asn Arg Thr Pro His
                85                  90

<210> SEQ ID NO 36
<211> LENGTH: 9
<212> TYPE: PRT
<213> ORGANISM: Homo sapiens

<400> SEQUENCE: 36

Ser Glu Arg Arg Ala Val Tyr Ile Gly
1               5

<210> SEQ ID NO 37

```
<211> LENGTH: 18
<212> TYPE: PRT
<213> ORGANISM: Homo sapien

<400> SEQUENCE: 37

Ser His Ser Pro His Leu Pro Arg Pro His Ser Arg Val Pro Pro His
1               5                   10                  15

Pro Ser

<210> SEQ ID NO 38
<211> LENGTH: 24
<212> TYPE: PRT
<213> ORGANISM: Homo sapien

<400> SEQUENCE: 38

Ala Trp Gly Trp Ala Arg Gly Ala Pro Arg Pro Pro Ser Ser Pro
1               5                   10                  15

Pro Leu Ser Ile Met Gly Leu Met
            20

<210> SEQ ID NO 39
<211> LENGTH: 100
<212> TYPE: PRT
<213> ORGANISM: Homo sapiens

<400> SEQUENCE: 39

Ala Leu Phe Pro Met Ser Gly Gly Trp Pro Gly Gly Gln Ala Cys Gln
1               5                   10                  15

Pro Ala Val Glu Met Ala Leu Glu Asp Val Asn Ser Arg Arg Asp Ile
                20                  25                  30

Leu Pro Asp Tyr Glu Leu Lys Leu Ile His His Asp Ser Lys Cys Asp
            35                  40                  45

Pro Gly Gln Ala Thr Lys Tyr Leu Tyr Glu Leu Leu Tyr Asn Asp Pro
        50                  55                  60

Ile Lys Ile Ile Leu Met Pro Gly Cys Ser Ser Val Ser Thr Leu Val
65                  70                  75                  80

Ala Glu Ala Ala Arg Met Trp Asn Leu Ile Val Leu Ser Tyr Gly Ser
                85                  90                  95

Ser Ser Pro Ala
            100

<210> SEQ ID NO 40
<211> LENGTH: 100
<212> TYPE: PRT
<213> ORGANISM: Homo sapiens

<400> SEQUENCE: 40

Pro Leu Thr Lys Glu Val Ala Lys Gly Ser Ile Gly Arg Gly Val Leu
1               5                   10                  15

Pro Ala Val Glu Leu Ala Ile Glu Gln Ile Arg Asn Glu Ser Leu Leu
                20                  25                  30

Arg Pro Tyr Phe Leu Asp Leu Arg Leu Tyr Asp Thr Glu Cys Asp Asn
            35                  40                  45

Ala Lys Gly Leu Lys Ala Phe Tyr Asp Ala Ile Lys Tyr Gly Pro Asn
        50                  55                  60

His Leu Met Val Phe Gly Gly Val Cys Pro Ser Val Thr Ser Ile Ile
65                  70                  75                  80

Ala Glu Ser Leu Gln Gly Trp Asn Leu Val Gln Leu Ser Phe Ala Ala
                85                  90                  95
```

Thr Thr Pro Val
            100

<210> SEQ ID NO 41
<211> LENGTH: 101
<212> TYPE: PRT
<213> ORGANISM: Homo sapien

<400> SEQUENCE: 41

Leu Ser Asn Arg Gln Arg Phe Pro Thr Phe Arg Thr His Pro Ser
 1               5                  10                  15

Ala Thr Leu His Asn Pro Thr Arg Val Lys Leu Phe Glu Lys Trp Gly
            20                  25                  30

Trp Lys Lys Ile Ala Thr Ile Gln Gln Thr Thr Glu Val Phe Thr Ser
        35                  40                  45

Thr Leu Asp Asp Leu Glu Glu Arg Val Lys Glu Ala Gly Ile Glu Ile
    50                  55                  60

Thr Phe Arg Gln Ser Phe Phe Ser Asp Pro Ala Val Pro Val Lys Asn
65                  70                  75                  80

Leu Lys Arg Gln Asp Ala Arg Ile Ile Val Gly Leu Phe Tyr Glu Thr
                85                  90                  95

Glu Ala Arg Lys Val
            100

<210> SEQ ID NO 42
<211> LENGTH: 101
<212> TYPE: PRT
<213> ORGANISM: Homo Sapien

<400> SEQUENCE: 42

Leu Ala Asp Lys Lys Lys Tyr Pro Tyr Phe Arg Thr Val Pro Ser
 1               5                  10                  15

Asp Asn Ala Val Asn Pro Ala Ile Leu Lys Leu Lys His Tyr Gln
            20                  25                  30

Trp Lys Arg Val Gly Thr Leu Thr Gln Asp Val Gln Arg Phe Ser Glu
        35                  40                  45

Val Arg Asn Asp Leu Thr Gly Val Leu Tyr Gly Glu Asp Ile Glu Ile
    50                  55                  60

Ser Asp Thr Glu Ser Phe Ser Asn Asp Pro Cys Thr Ser Val Lys Lys
65                  70                  75                  80

Leu Lys Gly Asn Asp Val Arg Ile Ile Leu Gly Gln Phe Asp Gln Asn
                85                  90                  95

Met Ala Ala Lys Val
            100

<210> SEQ ID NO 43
<211> LENGTH: 97
<212> TYPE: PRT
<213> ORGANISM: Homo sapien

<400> SEQUENCE: 43

Phe Cys Glu Val Tyr Lys Glu Arg Leu Phe Gly Lys Lys Tyr Val Trp
 1               5                  10                  15

Phe Leu Ile Gly Trp Tyr Ala Asp Asn Trp Phe Lys Ile Tyr Asp Pro
            20                  25                  30

Ser Ile Asn Cys Thr Val Asp Glu Met Thr Glu Ala Val Glu Gly His
        35                  40                  45

-continued

Ile Thr Thr Glu Ile Val Met Leu Asn Pro Ala Asn Thr Arg Ser Ile
            50                  55                  60

Ser Asn Met Thr Ser Gln Glu Phe Val Glu Lys Leu Thr Lys Arg Leu
65                  70                  75                  80

Lys Arg His Pro Glu Glu Thr Gly Gly Phe Gln Glu Ala Pro Leu Ala
                85                  90                  95

Tyr

<210> SEQ ID NO 44
<211> LENGTH: 96
<212> TYPE: PRT
<213> ORGANISM: Homo sapien

<400> SEQUENCE: 44

Phe Cys Cys Ala Tyr Glu Glu Asn Met Tyr Gly Ser Lys Tyr Gln Trp
1               5                   10                  15

Ile Ile Pro Gly Trp Tyr Glu Pro Ser Trp Glu Gln Val His Thr
                20                  25                  30

Glu Ala Asn Ser Ser Arg Cys Leu Arg Lys Asn Leu Leu Ala Ala Met
                35                  40                  45

Glu Gly Tyr Ile Gly Val Asp Phe Glu Pro Leu Ser Ser Lys Gln Ile
            50                  55                  60

Lys Thr Ile Ser Gly Lys Thr Pro Gln Gln Tyr Glu Arg Glu Tyr Asn
65                  70                  75                  80

Asn Lys Arg Ser Gly Val Gly Pro Ser Lys Phe His Gly Tyr Ala Tyr
                85                  90                  95

<210> SEQ ID NO 45
<211> LENGTH: 99
<212> TYPE: PRT
<213> ORGANISM: Homo sapien

<400> SEQUENCE: 45

Asp Ala Ile Trp Ala Leu Ala Leu Asn Lys Thr Ser Gly Gly
1               5                   10                  15

Gly Gly Arg Ser Gly Val Arg Leu Glu Asp Phe Asn Tyr Asn Asn Gln
                20                  25                  30

Thr Ile Thr Asp Gln Ile Tyr Arg Ala Met Asn Ser Ser Ser Phe Glu
            35                      40                  45

Gly Val Ser Gly His Val Val Phe Asp Ala Ser Gly Ser Arg Met Ala
50                  55                  60

Trp Thr Leu Ile Glu Gln Pro Gln Gly Gly Ser Tyr Lys Lys Ile Gly
65                  70                  75                  80

Tyr Tyr Asp Ser Thr Lys Asp Asp Leu Ser Trp Ser Lys Thr Asp Lys
                85                  90                  95

Trp Ile Gly

<210> SEQ ID NO 46
<211> LENGTH: 100
<212> TYPE: PRT
<213> ORGANISM: Homo sapien

<400> SEQUENCE: 46

Asp Gly Ile Trp Val Ile Ala Lys Thr Leu Gln Arg Ala Met Glu Thr
1               5                   10                  15

Leu His Ala Ser Ser Arg His Gln Arg Ile Gln Asp Phe Asn Tyr Thr
                20                  25                  30

-continued

Asp His Thr Leu Gly Arg Ile Ile Leu Asn Ala Met Asn Glu Thr Asn
        35                  40                  45

Phe Phe Gly Val Thr Gly Gln Val Val Phe Arg Asn Gly Glu Arg Met
    50                  55                  60

Gly Thr Ile Lys Phe Thr Gln Phe Gln Asp Ser Arg Glu Val Lys Val
65                  70                  75                  80

Gly Glu Tyr Asn Ala Val Ala Asp Thr Leu Glu Ile Ile Asn Asp Thr
                85                  90                  95

Ile Arg Phe Gln
            100

<210> SEQ ID NO 47
<211> LENGTH: 101
<212> TYPE: PRT
<213> ORGANISM: Homo sapien

<400> SEQUENCE: 47

Gly Ser Pro Pro Ala Asp Gln Thr Leu Val Ile Lys Thr Phe Arg Phe
1               5                   10                  15

Leu Ser Gln Lys Leu Phe Ile Ser Val Ser Val Leu Ser Ser Leu Gly
                20                  25                  30

Ile Val Leu Ala Val Val Cys Leu Ser Phe Asn Ile Tyr Asn Ser His
            35                  40                  45

Val Arg Tyr Ile Gln Asn Ser Gln Pro Asn Leu Asn Asn Leu Thr Ala
    50                  55                  60

Val Gly Cys Ser Leu Ala Leu Ala Ala Val Phe Pro Leu Gly Leu Asp
65                  70                  75                  80

Gly Tyr His Ile Gly Arg Asn Gln Phe Pro Phe Val Cys Gln Ala Arg
                85                  90                  95

Leu Trp Leu Leu Gly
            100

<210> SEQ ID NO 48
<211> LENGTH: 102
<212> TYPE: PRT
<213> ORGANISM: Homo sapien

<400> SEQUENCE: 48

Gly Ser Glu Pro Pro Lys Asp Lys Thr Ile Ile Leu Glu Gln Leu Arg
1               5                   10                  15

Lys Ile Ser Leu Pro Leu Tyr Ser Ile Leu Ser Ala Leu Thr Ile Leu
                20                  25                  30

Gly Met Ile Met Ala Ser Ala Phe Leu Phe Asn Ile Lys Asn Arg
            35                  40                  45

Asn Gln Lys Leu Ile Lys Met Ser Ser Pro Tyr Met Asn Asn Leu Ile
    50                  55                  60

Ile Leu Gly Gly Met Leu Ser Tyr Ala Ser Ile Phe Leu Phe Gly Leu
65                  70                  75                  80

Asp Gly Ser Phe Val Ser Glu Lys Thr Phe Glu Thr Leu Cys Thr Val
                85                  90                  95

Arg Thr Trp Ile Leu Thr
            100

<210> SEQ ID NO 49
<211> LENGTH: 102
<212> TYPE: PRT
<213> ORGANISM: Homo sapien -continued

```
<400> SEQUENCE: 49

Leu Gly Phe Ser Leu Gly Tyr Gly Ser Met Phe Thr Lys Ile Trp Trp
 1               5                  10                  15

Val His Thr Gly Phe Thr Lys Lys Glu Lys Lys Glu Trp Arg Lys
                20                  25                  30

Thr Leu Glu Pro Trp Lys Leu Tyr Ala Thr Val Gly Leu Leu Val Gly
            35                  40                  45

Met Asp Val Leu Thr Leu Ala Ile Trp Gln Ile Val Asp Pro Leu His
 50                  55                  60

Arg Thr Ile Glu Thr Phe Ala Lys Glu Glu Pro Lys Glu Asp Ile Asp
 65                  70                  75                  80

Val Ser Ile Leu Pro Gln Leu Glu His Cys Ser Ser Arg Lys Met Asn
                 85                  90                  95

Thr Trp Leu Gly Ile Phe
                100

<210> SEQ ID NO 50
<211> LENGTH: 99
<212> TYPE: PRT
<213> ORGANISM: Homo sapien

<400> SEQUENCE: 50

Val Gly Tyr Thr Thr Ala Phe Gly Ala Met Phe Ala Lys Thr Trp Arg
 1               5                  10                  15

Val His Ala Ile Phe Lys Asn Val Lys Met Lys Lys Ile Ile Lys
                20                  25                  30

Asp Gln Lys Leu Leu Val Ile Val Gly Gly Met Leu Leu Ile Asp Leu
            35                  40                  45

Cys Ile Leu Ile Cys Trp Gln Ala Val Asp Pro Leu Arg Arg Thr Val
 50                  55                  60

Glu Lys Tyr Ser Met Glu Pro Asp Pro Ala Gly Arg Asp Ile Ser Ile
 65                  70                  75                  80

Arg Pro Leu Leu Glu His Cys Glu Asn Thr His Met Thr Ile Trp Leu
                 85                  90                  95

Gly Ile Val

<210> SEQ ID NO 51
<211> LENGTH: 92
<212> TYPE: PRT
<213> ORGANISM: Homo sapien

<400> SEQUENCE: 51

Tyr Gly Tyr Lys Gly Leu Leu Leu Leu Gly Ile Phe Leu Ala Tyr
 1               5                  10                  15

Glu Thr Lys Ser Val Ser Thr Glu Lys Ile Asn Asp His Arg Ala Val
                20                  25                  30

Gly Met Ala Ile Tyr Asn Val Ala Val Leu Cys Leu Ile Thr Ala Pro
            35                  40                  45

Val Thr Met Ile Leu Ser Ser Gln Gln Asp Ala Ala Phe Ala Phe Ala
 50                  55                  60

Ser Leu Ala Ile Val Phe Ser Ser Tyr Ile Thr Leu Val Leu Phe
 65                  70                  75                  80

Val Pro Lys Met Arg Arg Leu Ile Thr Arg Gly Glu
                 85                  90

<210> SEQ ID NO 52
```

-continued

```
<211> LENGTH: 99
<212> TYPE: PRT
<213> ORGANISM: Homo sapien

<400> SEQUENCE: 52

Tyr Ala Tyr Lys Gly Leu Leu Met Leu Phe Gly Cys Phe Leu Ala Trp
1               5                   10                  15

Glu Thr Arg Asn Val Ser Ile Pro Ala Leu Asn Asp Ser Lys Tyr Ile
            20                  25                  30

Gly Met Ser Val Tyr Asn Val Gly Ile Met Cys Ile Ile Gly Ala Ala
        35                  40                  45

Val Ser Phe Leu Thr Arg Asp Gln Pro Asn Val Gln Phe Cys Ile Val
    50                  55                  60

Ala Leu Val Ile Ile Phe Cys Ser Thr Ile Thr Leu Cys Leu Val Phe
65                  70                  75                  80

Val Pro Lys Leu Ile Thr Leu Arg Thr Asn Pro Asp Ala Ala Thr Gln
                85                  90                  95

Asn Arg Arg

<210> SEQ ID NO 53
<211> LENGTH: 96
<212> TYPE: PRT
<213> ORGANISM: Homo sapien

<400> SEQUENCE: 53

Trp Gln Ser Glu Ala Gln Asp Thr Met Lys Thr Gly Ser Ser Thr Asn
1               5                   10                  15

Asn Asn Glu Glu Glu Lys Ser Arg Leu Leu Glu Lys Glu Asn Arg Glu
            20                  25                  30

Leu Glu Lys Ile Ile Ala Glu Lys Glu Glu Arg Val Ser Glu Leu Arg
        35                  40                  45

His Gln Leu Gln Ser Arg Gln Gln Leu Arg Ser Arg Arg His Pro Pro
    50                  55                  60

Thr Pro Pro Glu Pro Ser Gly Leu Pro Arg Gly Pro Pro Glu Pro
65                  70                  75                  80

Pro Asp Arg Leu Ser Cys Asp Gly Ser Arg Val His Leu Leu Tyr Lys
                85                  90                  95

<210> SEQ ID NO 54
<211> LENGTH: 102
<212> TYPE: PRT
<213> ORGANISM: Homo sapien

<400> SEQUENCE: 54

Phe Gln Phe Thr Gln Asn Gln Lys Lys Glu Asp Ser Lys Thr Ser Thr
1               5                   10                  15

Ser Val Thr Ser Val Asn Gln Ala Ser Thr Ser Arg Leu Glu Gly Leu
            20                  25                  30

Gln Ser Glu Asn His Arg Leu Arg Met Lys Ile Thr Glu Leu Asp Lys
        35                  40                  45

Asp Leu Glu Glu Val Thr Met Gln Leu Gln Asp Thr Pro Glu Lys Thr
    50                  55                  60

Thr Tyr Ile Lys Gln Asn His Tyr Gln Glu Leu Asn Asp Ile Leu Asn
65                  70                  75                  80

Leu Gly Asn Phe Thr Glu Ser Thr Asp Gly Gly Lys Ala Ile Leu Lys
                85                  90                  95

Asn His Leu Asp Gln Asn
```

```
<210> SEQ ID NO 55
<211> LENGTH: 80
<212> TYPE: PRT
<213> ORGANISM: Homo sapien

<400> SEQUENCE: 55

Pro Gln Leu Gln Trp Asn Thr Thr Glu Pro Ser Arg Thr Cys Lys Asp
 1               5                  10                  15

Pro Ile Glu Asp Ile Asn Ser Pro Glu His Ile Gln Arg Arg Leu Ser
            20                  25                  30

Leu Gln Leu Pro Ile Leu His His Ala Tyr Leu Pro Ser Ile Gly Gly
        35                  40                  45

Val Asp Ala Ser Cys Val Ser Pro Cys Val Ser Pro Thr Ala Ser Pro
    50                  55                  60

Arg His Arg His Val Pro Pro Ser Phe Arg Val Met Val Ser Gly Leu
65                  70                  75                  80
```

RECEPTOR

CROSS REFERENCE TO RELATED APPLICATIONS

This U.S. patent application claims priority to GB9819420.2 filed on Sep. 7, 1998 in the United Kingdom and to U.S. provisional application No. 60/103,670 filed on Oct. 9, 1998 in the United States Patent Office.

FIELD OF THE INVENTION

The present invention relates to the novel $GABA_B$ receptor subtypes $GABA_B$-R1c and $GABA_B$-R2 as well as to a novel, functional $GABA_B$ receptor which comprises a heterodimer of $GABA_B$-R1 and $GABA_B$-R2 receptor subunits. The present invention also relates to variants of the receptors, nucleotide sequences encoding the receptors and variants thereof and novel vectors, stable cell lines, antibodies, screening methods, methods of treatment and methods of receptor production.

BACKGROUND OF THE INVENTION

GABA (γ-amino-butyric acid) is the main inhibitory neurotransmitter in the central nervous system (CNS) activating two distinct families of receptors; the ionotropic $GABA_A$ and $GABA_C$ receptors for fast synaptic transmissions, and the metabotropic $GABA_B$ receptors governing a slower synaptic transmission. $GABA_B$ receptors are members of the superfamily of 7-transmembrane G protein-coupled receptors. Activation results in signal transduction through a variety of pathways mediated principally via members of the $G_i/G_o$ family of pertussis toxin-sensitive G proteins. $GABA_B$ receptors have been shown to inhibit N, P/Q and T-type $Ca^{2+}$ channels in a pertussis toxin-sensitive manner (Kobrinsky et al., 1993; Menon-Johansson et al., 1993; Harayama et al., 1998) and indeed there is also some evidence for direct interactions between $GABA_B$ receptors and $Ca^{2+}$ channels since $Ca^{2+}$ channel ligands can modify the binding of $GABA_B$ agonists (Ohmori et al., 1990). $GABA_B$ receptor-mediated $Ca^{2+}$ channel inhibition is the principle mechanism for presynaptic inhibition of neurotransmitter release. Post-synaptically the major effect of $GABA_B$ receptor activation is to open potassium channels, to generate post-synaptic inhibitory potentials. Autoradiographic studies show that $GABA_B$ receptors are abundant and heterogeneously distributed throughout the CNS, with particularly high levels in the molecular layer of the cerebellum, interpeduncular nucleus, frontal cortex, olfactory nuclei and thalamic nuclei. $GABA_B$ receptors are also widespread in the globus pallidus, temporal cortex, raphe magnus and spinal cord (Bowery et al., 1987). $GABA_B$ receptors are an important therapeutic target in the CNS for conditions such as spasticity, epilepsy, Alzheimer's disease, pain, affective disorders and feeding. $GABA_B$ receptors are also present in the peripheral nervous system, both on sensory nerves and on parasympathetic nerves. Their ability to modulate these nerves gives them potential as targets in disorders of the lung, GI tract and bladder (Kerr and Ong, 1995; 1996; Malcangio and Bowery, 1995).

Despite the widespread abundance of $GABA_B$ receptors, considerable evidence from neurochemical, electrophysiological and behavioural studies suggests that multiple subtypes of $GABA_B$ receptors exist. This heterogeneity of $GABA_B$ receptors may allow the development of selective ligands, able to target specific aspects of $GABA_B$ receptor function. This would lead to the development of drugs with improved selectivity profiles relative to current compounds (such as baclofen) which are relatively non-selective and show a variety of undesirable behavioural actions such as sedation and respiratory depression. Multiple receptor subtypes are best classified by the differing profiles of agonist and antagonist ligands.

To date screening for $GABA_B$ ligands and subsequent structure/activity determinations has relied on radioligand binding assays to rat brain membranes. Further analysis of such ligands in animal models has indicated differences in their behavioural profile. However, due to the absence of cloned $GABA_B$ receptors the molecular basis for such differences has not been defined, and therefore it has not been possible to optimise $GABA_B$ ligands for therapeutic use.

$GABA_B$ receptors were first described nearly 20 years ago (Hill and Bowery, 1981), but despite extensive efforts using conventional expression cloning strategies, for example in Xenopus oocytes, or cloning based on sequence homology, the molecular nature of the $GABA_B$ receptor remained elusive. The development of a high affinity antagonist for the receptor finally allowed Kaupmann et al, (1997) to expression clone the receptor from a rat cerebral cortex cDNA using a radioligand binding assay. Two splice variants of the receptor were identified, $GABA_B$-R1a encoding a 960 amino acid protein and $GABA_B$-R1b, encoding an 844 amino acid protein, differing only in the lengths of their N-termini. These two splice variants have distinct spatial distributions within the brain, but both reside within neuronal rather than glial cells. Pharmacologically, the two splice variants are similar, showing binding affinities for a range of antagonists, but about 10 fold lower than those of native receptors, as well as agonist displacement constants which are about 100–150 a fold lower than those of native receptors. These observations have led to speculation that the cloned receptor was a low affinity receptor and an additional high affinity, pharmacologically distinct $GABA_B$ receptor subtype could exist in the brain. Alternatively, it was argued that G-protein coupling was inefficient or the receptor was desensitising in the recombinant systems used.

A number of groups working in the area have, however, found that the cloned receptor fails to behave as a functional $GABA_B$ receptor either in mammalian cells or in Xenopus oocytes. The present invention describes the cloning of a novel human $GABA_B$ receptor subtype, $GABA_B$-R2, the identification of a novel splice variant $GABA_B$-R1c, and the surprising observation that $GABA_B$-R1 and $GABA_B$-R2 strongly interact via their C-termini to form heterodimers. Co-expression of $GABA_B$-R1 and $GABA_B$-R2 allows trafficking of $GABA_B$-R1 to the cell surface and results in a high affinity functional $GABA_B$ receptor in both mammalian cells and Xenopus oocytes.

These surpising findings provide a unique opportunity to define $GABA_B$ subtypes at the molecular level, which in turn will lead to the identification of novel subtype-specific drugs.

SUMMARY OF THE INVENTION

According to one embodiment of the present invention there is provided an isolated $GABA_B$-R2 receptor protein or a variant thereof.

According to another embodiment of the invention there is provided an isolated $GABA_B$-R2 receptor protein having amino acid sequence provided in FIG. 1B, or a variant thereof.

According to a further embodiment of the invention there is provided a nucleotide sequence encoding a $GABA_B$-R2 receptor or a variant thereof, or a nucleotide sequence which is complementary thereto.

According to a further embodiment of the invention there is provided a nucleotide sequence encoding a $GABA_B$-R2 receptor, as shown in FIG. 1A, or a variant thereof, or a nucleotide sequence which is complementary thereto.

According to a further embodiment of the invention there is provided an expression vector comprising a nucleotide sequence as referred to above which is capable of expressing a $GABA_B$-R2 receptor protein or a variant thereof.

According to a still further embodiment of the invention there is provided a stable cell line comprising a vector as referred to above.

According to another embodiment of the invention there is provided an antibody specific for a $GABA_B$-R2 receptor protein or a variant thereof.

According to another embodiment of the invention there is provided an isolated $GABA_B$-R1c receptor protein or a variant thereof.

According to another embodiment of the invention there is provided an isolated $GABA_B$-R1c receptor protein having amino acid sequence provided in FIG. 2, or a variant thereof.

According to another embodiment of the invention there is provided a nucleotide sequence encoding a $GABA_B$-R1c receptor protein or a variant thereof, or a nucleotide sequence which is complementary thereto.

According to another embodiment of the invention there is provided an expression vector comprising a nucleotide sequence as referred to above, which is capable of expressing a $GABA_B$-R1c receptor protein or a variant thereof.

According to another embodiment of the invention there is provided a stable cell line comprising a vector as referred to above.

According to a further embodiment of the invention there is provided an antibody specific for a $GABA_B$-R1c receptor protein or a variant thereof.

According to a further embodiment of the invention there is provided a $GABA_B$ receptor comprising an heterodimer between a $GABA_B$-R1 receptor protein or a variant thereof and a $GABA_B$-R2 receptor protein or a variant thereof.

According to a further embodiment of the invention there is provided an expression vector comprising a nucleotide sequence encoding for a $GABA_B$-R1 receptor or a variant thereof and a nucleotide sequence encoding for a $GABA_B$-R2 receptor or variant thereof, said vector being capable of expressing both $GABA_B$-R1 and $GABA_B$-R2 receptor proteins or variants thereof.

According to a further embodiment of the invention there is provided a stable cell line comprising a vector as referred to above.

According to a further embodiment of the invention there is provided a stable cell line modified to express both $GABA_B$-R1 and $GABA_B$-R2 receptor proteins or variants thereof.

According to a further embodiment of the invention there is provided a $GABA_B$ receptor produced by a stable cell line as referred to above.

According to a further embodiment of the invention there is provided an antibody specific for a $GABA_B$ receptor as referred to above.

According to a further embodiment of the invention there is provided a method for identification of a compound which exhibits $GABA_B$ receptor modulating activity, comprising contacting a $GABA_B$ receptor as referred to above with a test compound and detecting modulating activity or inactivity.

According to a further embodiment of the invention there is provided a compound which modulates $GABA_B$ receptor activity, identifiable by a method as referred to above.

According to a further embodiment of the invention there is provided a method of treatment or prophylaxis of a disorder which is responsive to modulation of $GABA_B$ receptor activity in a mammal, which comprises administering to said mammal an effective amount of a compound identifiable by the method referred to above.

BRIEF DESCRIPTION OF THE FIGURES

FIGS. 1A-1, 1A-2 and 1B. Nucleotide and protein sequences of Human $GABA_B$-R2.

Nucleotide sequence (a) and the translated protein sequence (b) for Human $GABA_B$-R2 are shown.

FIGS. 2A–2C. Protein alignments between $GABA_B$-R1a, $GABA_B$-R1b, $GABA_B$-R1c splice variants and $GABA_B$-R2.

Amino-acid sequences of the human $GABA_B$-R1a, $GABA_B$-R1b and $GABA_B$-R2 receptors aligned for comparison. Signal sequences and predicted cleavage point ✕, together with the N-terminal splice points for $GABA_B$-R1a and $GABA_B$-R1b are shown. $GABA_B$-R1c sequence is exactly that of $GABA_B$-R1a, except for the deletion of 63 amino acids (open box). Amino acids conserved between $GABA_B$-R1a and $GABA_B$-R1b are in bold type and potential N-glycosylation sites (*) are shown. Lines beneath the text show positions of the seven predicted TM domains and regions encoding coiled coil structure are indicated by shading. The C-terminal region of $GABA_B$-R1 used as the bait in the yeast two hybrid analysis is marked as 'BAIT→', and $GABA_B$-R2 C-terminal domains recovered from the library screen against $GABA_B$-R1 C-terminus are shown as 'YTH HITS→'.

Figure 3:
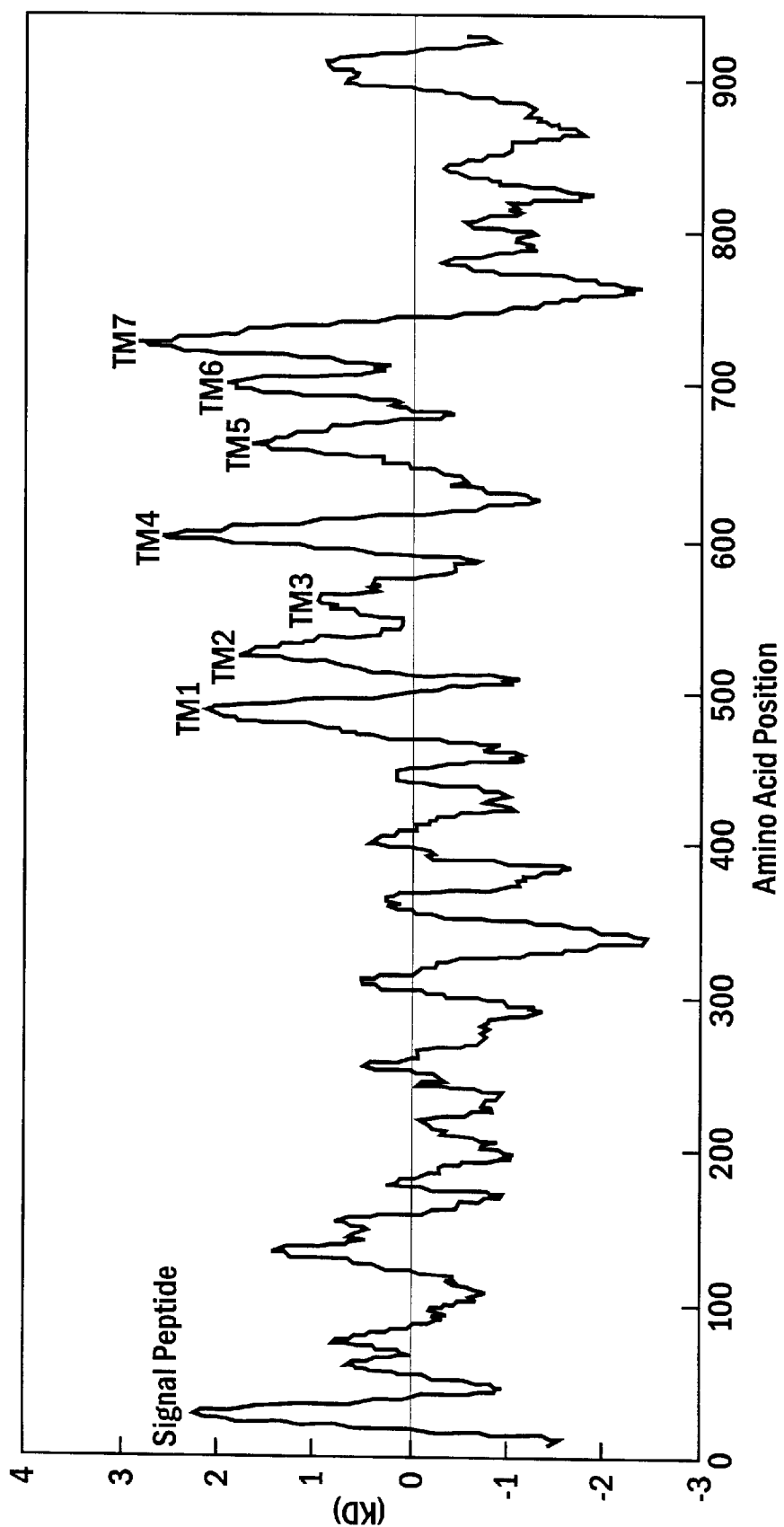

FIG. 3. Hydrophobicity profile of $GABA_B$-R2.

Hydrophobicity profiles of $GABA_B$-R2 sequence were determined using the Kyte-Doolittle algorithm, whereby positive values indicate hydrophobic regions. The predicted signal sequence and seven trans-membrane domains are shown.

Figure 4A:
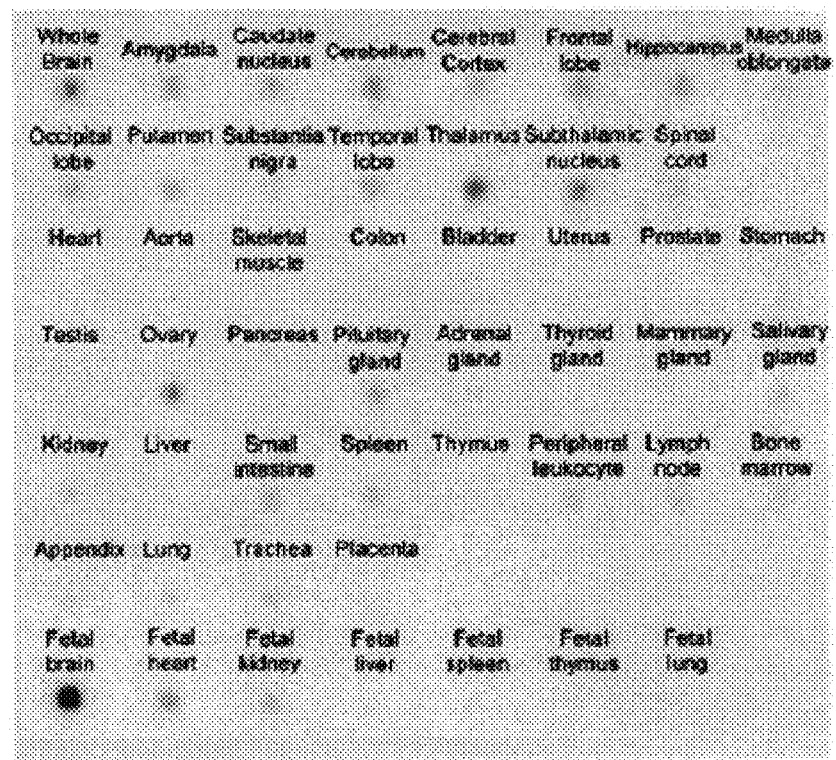
Figure 4B:
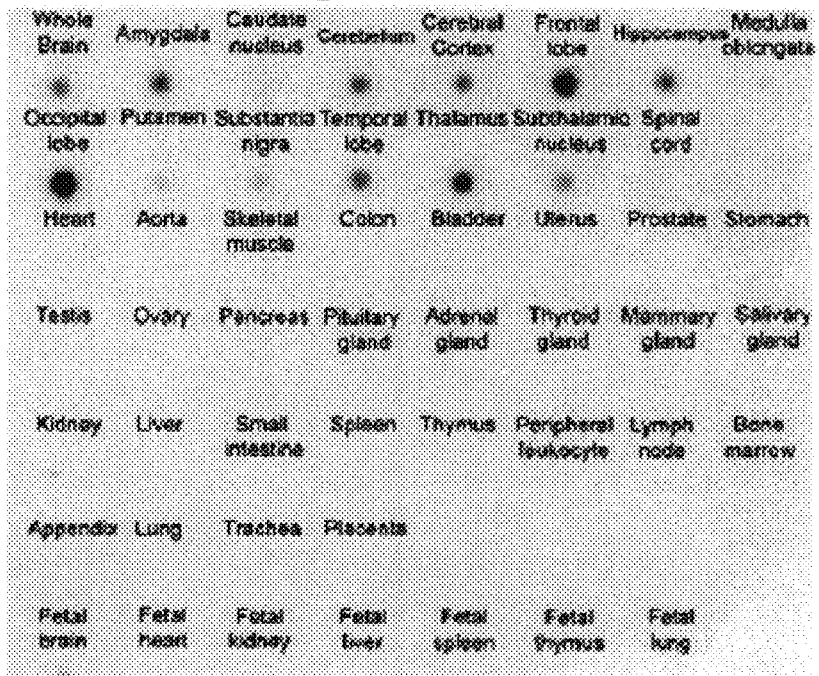

FIGS. 4A and 4B. Tissue Distribution Studies for Human $GABA_B$-R1 and $GABA_B$-R2.

A Human RNA Master Blot (Clontech), containing normalised polyA$^+$ mRNA from multiple tissues of adult and fetal origin, were probed sequentially with a pan specific probe for $GABA_B$-R1 (all splice variants) followed by a $GABA_B$-R2 specific probe. Resulting autoradiographic analysis of the blots are shown, together with a grid identifying tissue type. Specificity controls include yeast RNA and E. coli DNA.

Figure 5:
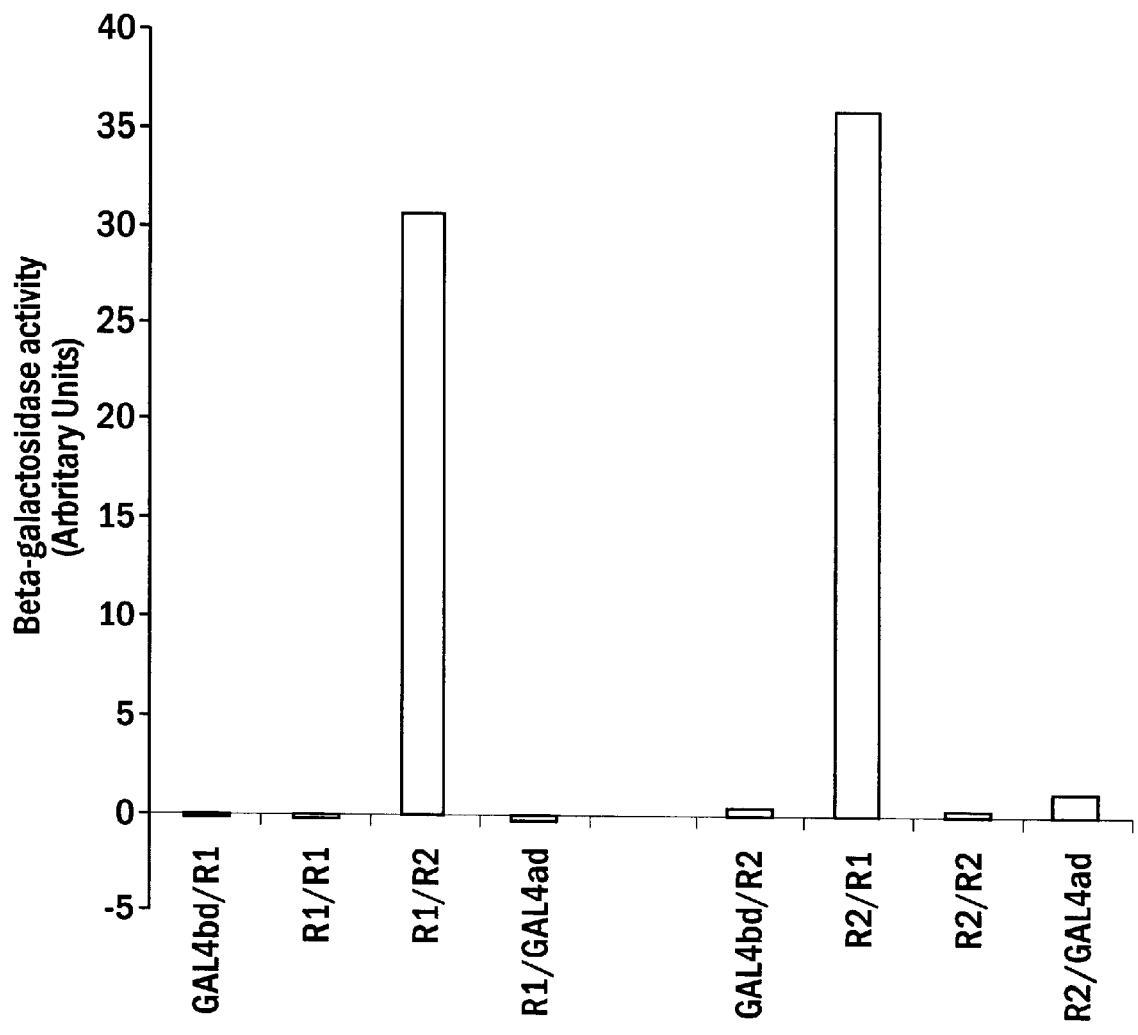

FIG. 5. Heterodimerisation and homodimerisation between the C-terminal domains of the $GABA_B$-R1 and $GABA_B$-R2 receptors in the yeast two hybrid system.

β-galactosidase activity was measured in yeast Y190 cells expressing the $GABA_B$-R1 or the $GABA_B$-R2 C-termini, either against empty vector or against each other in all combinations, using ONPG. Of each pair of proteins expressed in the two hybrid system, the first always refers to the $GAL4_{BD}$ fusion construct whilst the second refers to the $GAL4_{AD}$ fusion construct. β-galactosidase activity is determined relative to cell numbers and is in arbitary units.

Figure 6:
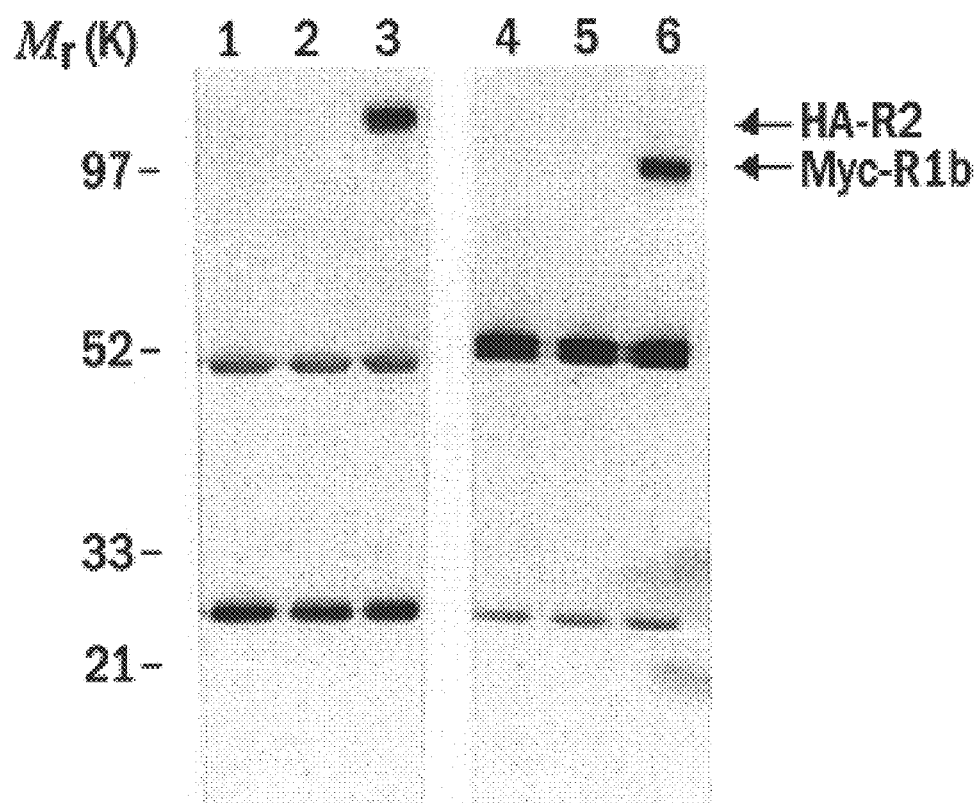

FIG. 6. Co-immunoprecipitation studies of the $GABA_B$ heterodimer in HEK239 cells.

HEK293T cells were transfected with 1 μg each of either Myc-$GABA_B$-R1b or HA-$GABA_B$-R2 alone or in combination. Cells were harvested 48 h after transfection, lysed and epitope tagged receptors immunoprecipitated using 12CA5 (HA) or 9E10 (Myc) antisera as described in Methods. Immune complexes were then subjected to SDS-PAGE, transferred to nitrocellulose, and captured Myc-GABA$_B$-R1b and HA-GABA$_B$-R2 identified by immunoblotting with Myc and HA, respectively. Lanes 1 and 4, immunoprecipitates of cells transfected with Myc-GABA$_B$-R1b only; lanes 2 and 5, HA-GABA$_B$-R2 only; lanes 3 and 6, immunoprecipitates of cells transfected with Myc-GABA$_B$-R1b together with HA-GABA$_B$-R2. Lanes 1–3, lysates immunoprecipitated with 9E10 (Myc) and blotted to 12CA5(HA); lanes 4–6, lysates immunoprecipitated with 12CA5(HA) and blotted with 9E10 (Myc)

FIG. 7. Cell surface localisation of GABA$_B$-R1 receptor is dependent upon coexpression with GABA$_B$-2.

Flow cytometry was performed on HEK293T cells transfected with 1 µg of either Myc-GABA$_B$-R1b or HA-GABA$_B$-R2 or both receptors in combination. (A) Analysis using 9E10 (c-Myc) as primary antibody to detect Myc-GABA$_B$-R1b; intact cells. (B) Analysis using 9E10 (c-Myc) as primary antibody to detect Myc-GABA$_B$-R1b; permeabilised cells. (C) Analysis using 12CA5 (HA) as primary antibody to detect HA-GABA$_B$-R2; intact cells. Mock transfected cells, reflecting background fluorescence, are shaded and the marker indicates fluorescence measured over background levels. Myc-GABA$_B$-R1b data is shown as a grey line whereas co-expression of Myc-GABA$_B$-R1b with HA-GABA$_B$-R2 is shown in black. 30,000 cells were analysed in each sample. Histograms shown are from a single experiment. Quoted statistics are from mean of three separate transfections and analysis.

Figure 8:
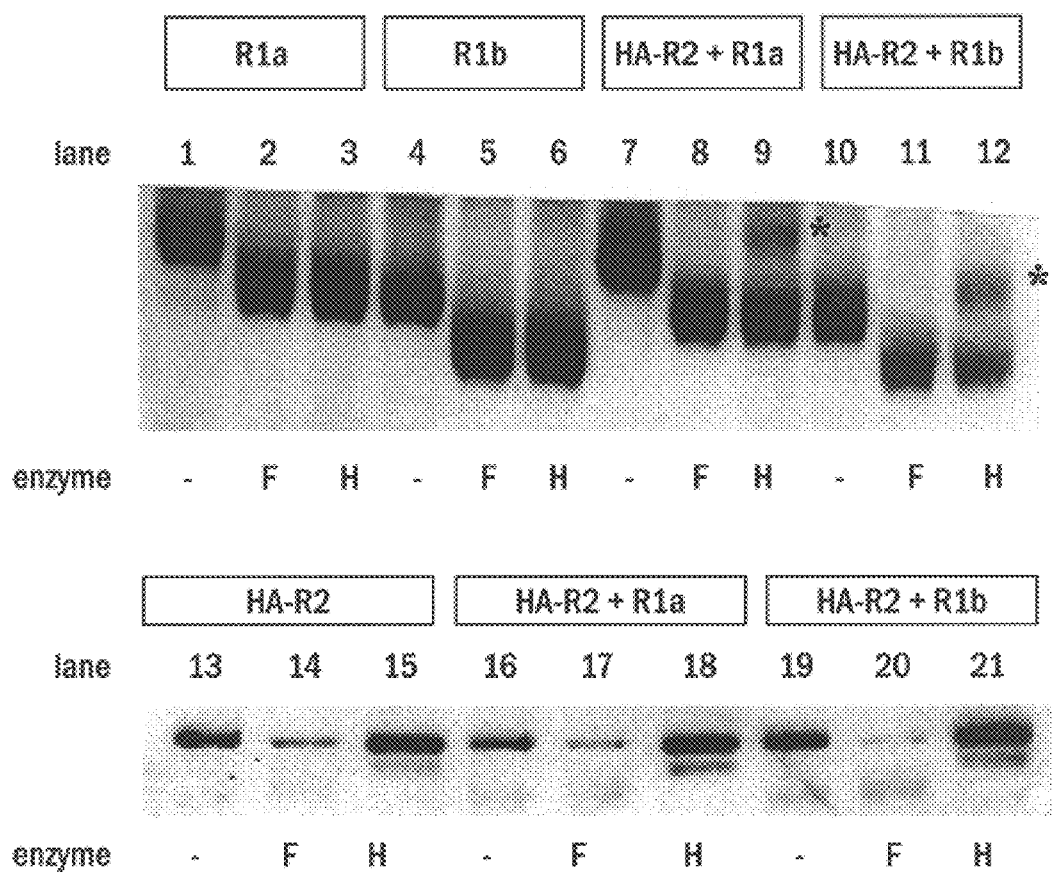

FIG. 8. Coexpression of GABA$_B$-R1a and 1b splice variants with GABA$_B$-R2 receptors in HEK293T cells results in terminal glycosylation of both GABA$_B$-R1a and GABA$_B$-R1b.

P2 membrane fractions were derived from HEK293T cells that were transfected with 1 µg of either GABA$_B$-R1a (lanes 1–3), GABA$_B$-R1b (lanes 4–6) or HA-GABA$_B$-R2 (lanes 13–15), or with 1 µg each of HA-GABA$_B$-R2 in combination with 1 µg of either GABA$_B$-R1a (lanes 7–9, 16–18) or GABA$_B$-R1b (lanes 10–12, 19–21). Glycosylation status of transfected receptors was assessed following treatment of P2 fractions (50 µg of membrane protein) with either vehicle (lanes 1, 4, 7, 10, 13, 16 and 19), endoglycosidase F (lanes 2, 5, 8, 11, 14, 17 and 20) or endoglycosidase H (lanes 3, 6, 9, 12, 15, 18 and 21). Samples were resolved by SDS-PAGE (10% (w/v) acrylamide), transferred to nitrocellulose, and immunoblotted. Upper panel, antiserum 501 was used as primary reagent to allow identification of both GABA$_B$-R1a and 1b. Lower panel, 12CA5 anti-HA antiserum was employed to identify HA-GABA$_B$-R2. *, denotes terminally glycosylated forms of GABA$_B$-R1a and 1b.

Figure 9A:
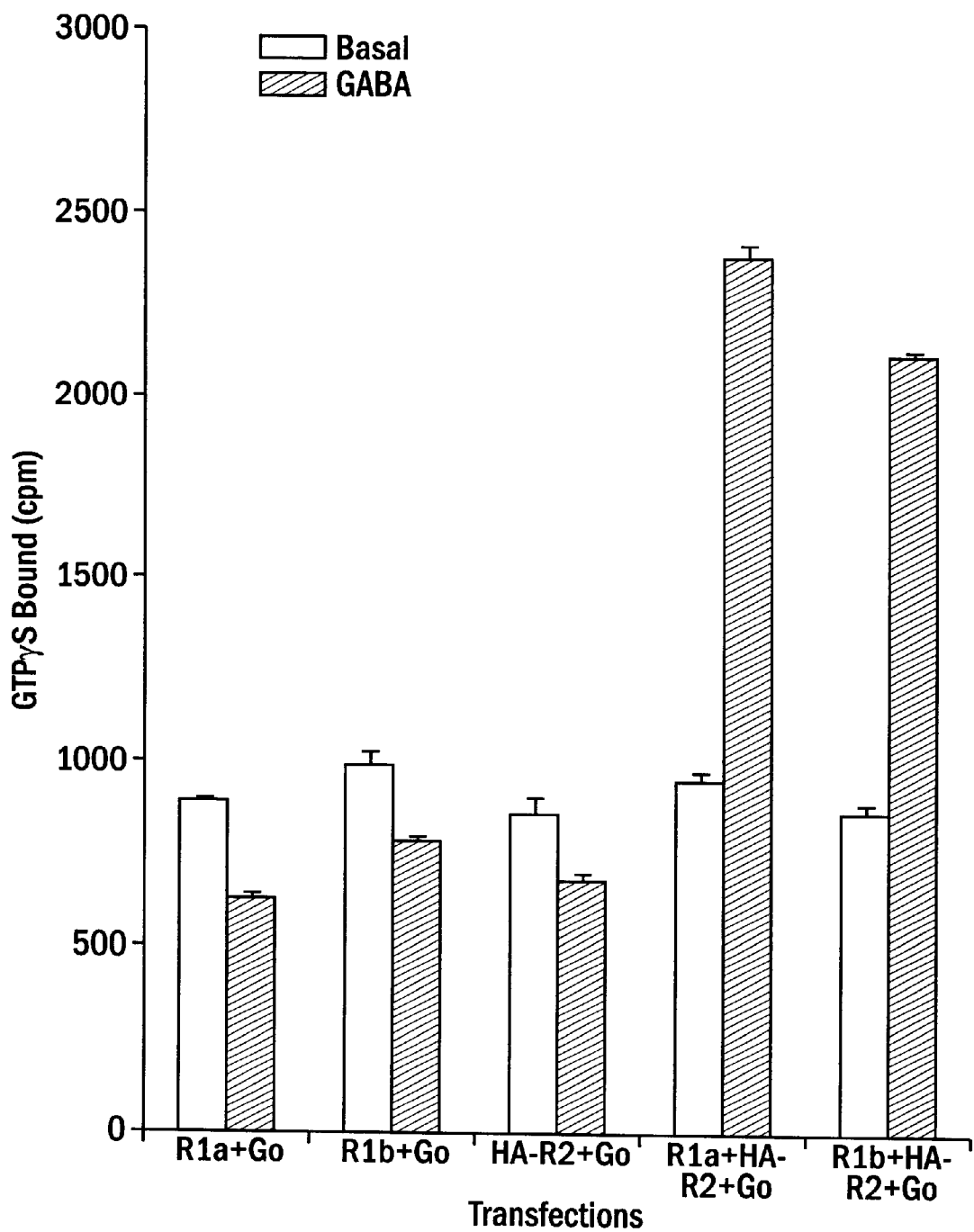
Figure 9B:
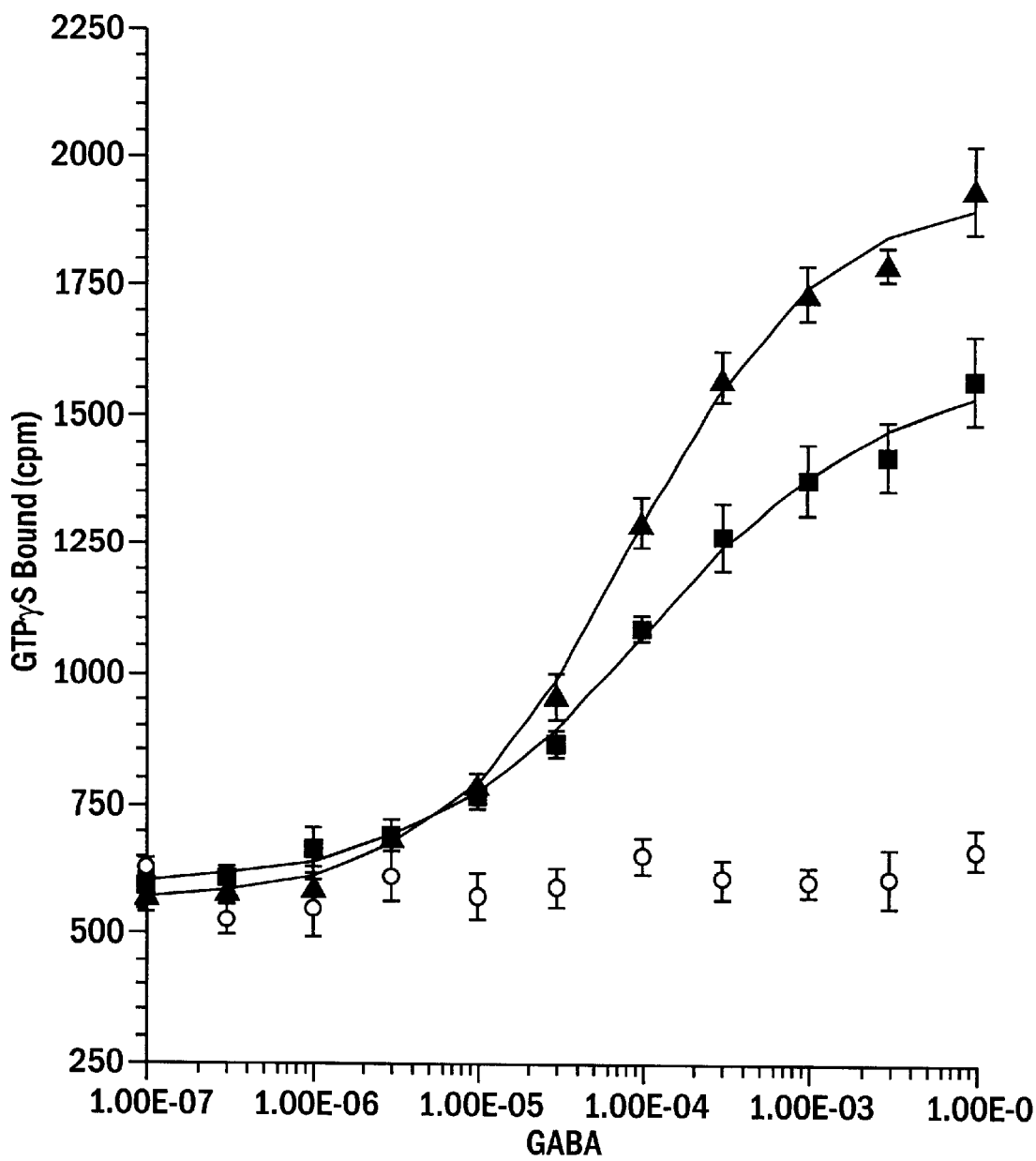

FIGS. 9A and 9B. Coexpression of GABA$_B$-R1 and GABA$_B$-R2 receptors in HEK293T cells leads to GABA-mediated stimulation of [$^{35}$S]GTPγS binding activity.

[$^{35}$S]GTPγS binding activity was measured on P2 particulate fractions derived from HEK293T cells transfected with 1 µg of G$_{o1}$α together with 1 µg of either GABA$_B$-R1a, GABA$_B$-R1b or HA-GABA$_B$-R2; or with 1 µg each of G$_{o1}$α and HA-GABA$_B$-R2 in combination with 1 µg of either GABA$_B$-R1a or GABA$_B$-R1b. (A) [$^{35}$S]GTPγS binding was measured in the absence (open bars) or presence (hatched bars) of GABA (10 mM) as described in Methods. (B) The ability of varying concentrations of GABA to stimulate the binding of [$^{35}$S]GTPγS was measured on P2 membrane fractions from HEK293T cells expressing either G$_{o1}$α and HA-GABA$_B$-R2 alone (open circles) or in combination with either GABA$_B$-R1a (closed squares) or GABA$_B$-R1b (closed triangles). The data shown are the means ±S.D. of triplicate measurements and are representative of three independent experiments.

Figure 10:
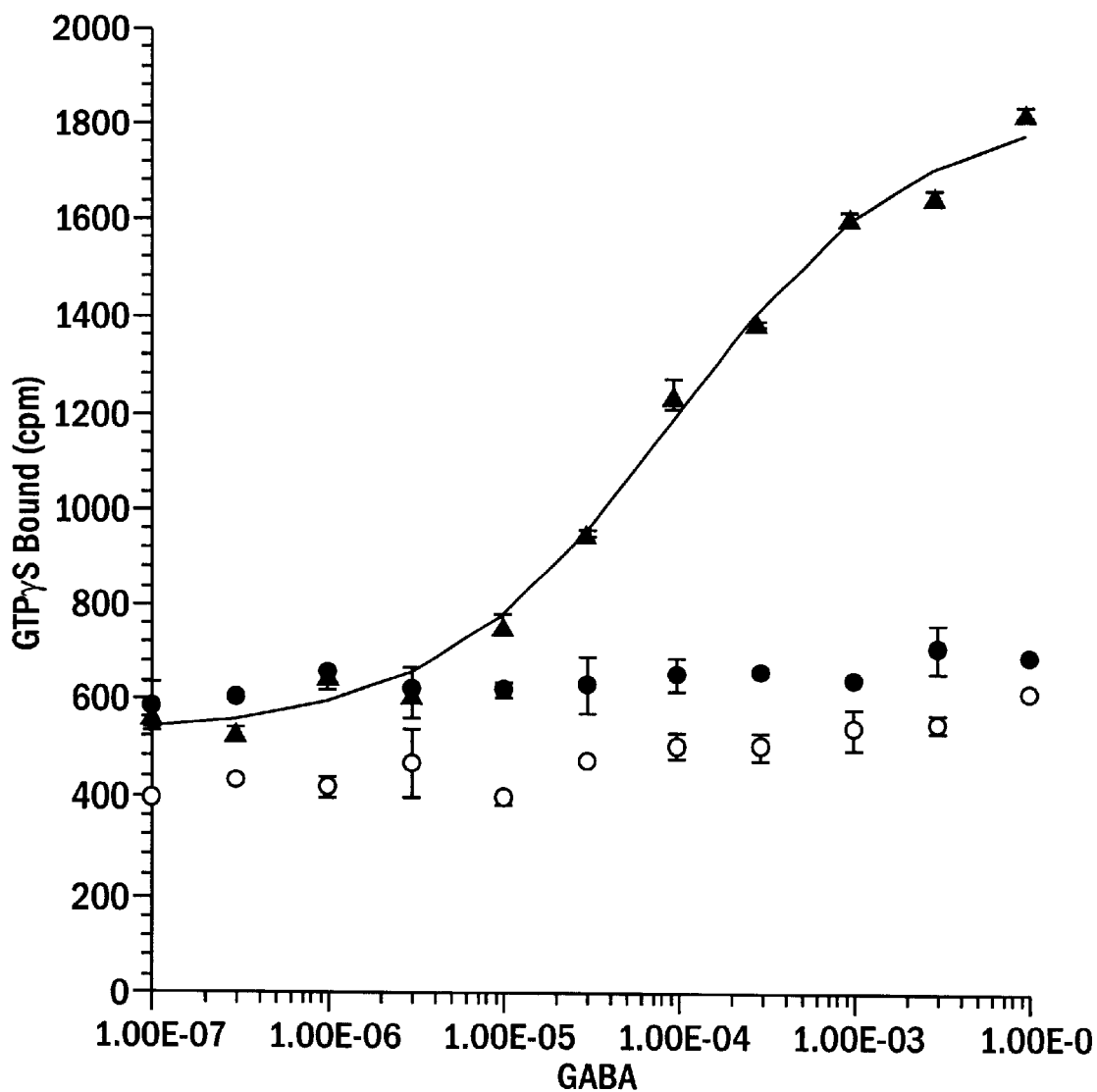

FIG. 10. GABA-mediated stimulation of [$^{35}$S]GTPγS binding activity in HEK293T cells coexpressing GABA$_B$-R1 and GABA$_B$-R2 receptors requires cotransfection with additional G$_i$G protein, G$_{o1}$α.

[$^{35}$S]GTPγS binding activity was measured on P2 particulate fractions derived from HEK293T cells transfected with HA-GABA$_B$-R1b (1 µg) together with HA-GABA$_B$-R2 (1 µg) and G$_{o1}$α (1 µg) (closed triangles), or in combination with either HA-GABA$_B$-R2 (1 µg) (open circles) or G$_{o1}$α (1 µg) (closed circles). The ability of varying concentrations of GABA to stimulate the binding of [$^{35}$S]GTPγS was determined. Data shown are the mean ±S.D. of triplicate measurements.

Figure 11A:
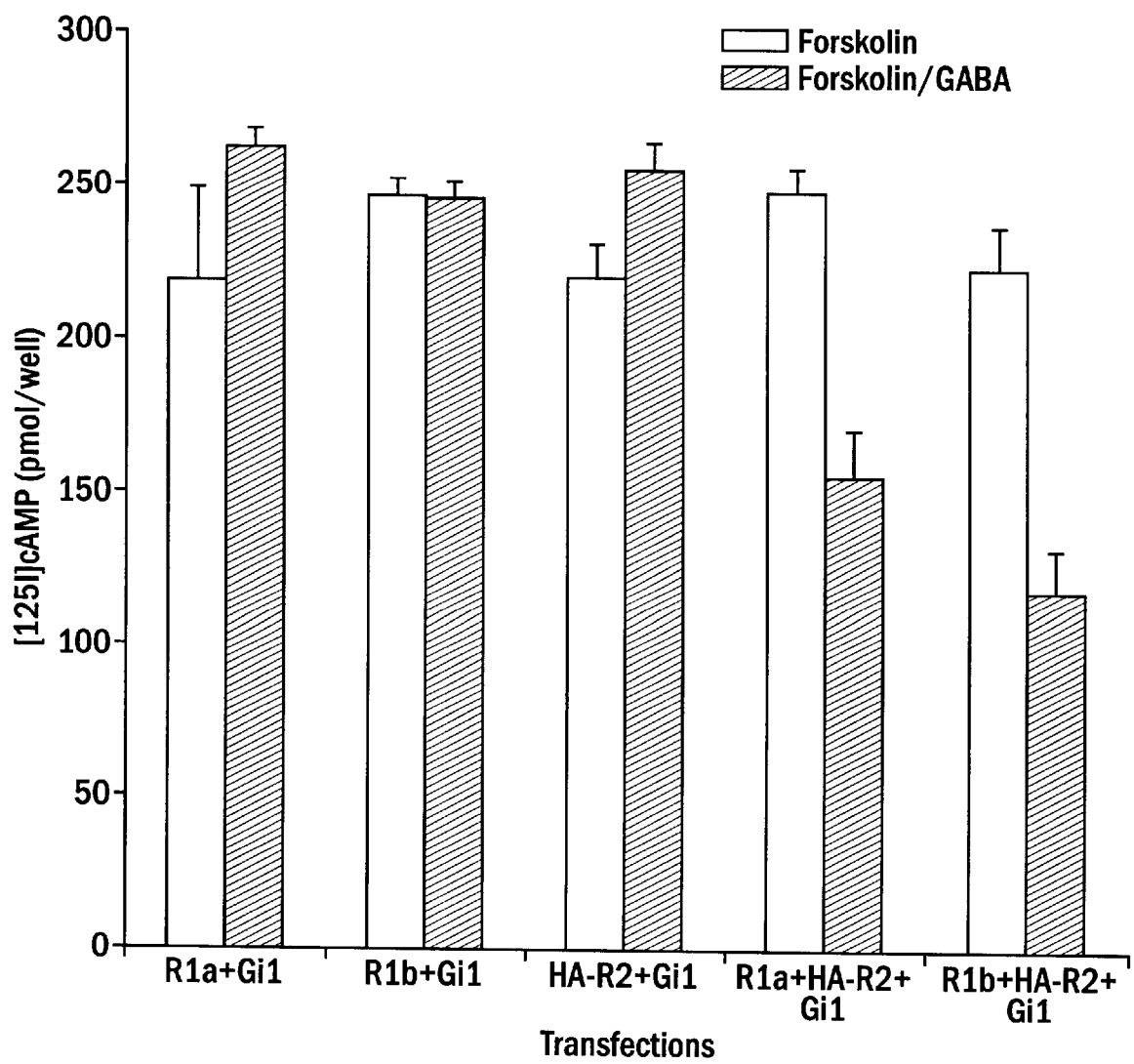
Figure 11B:
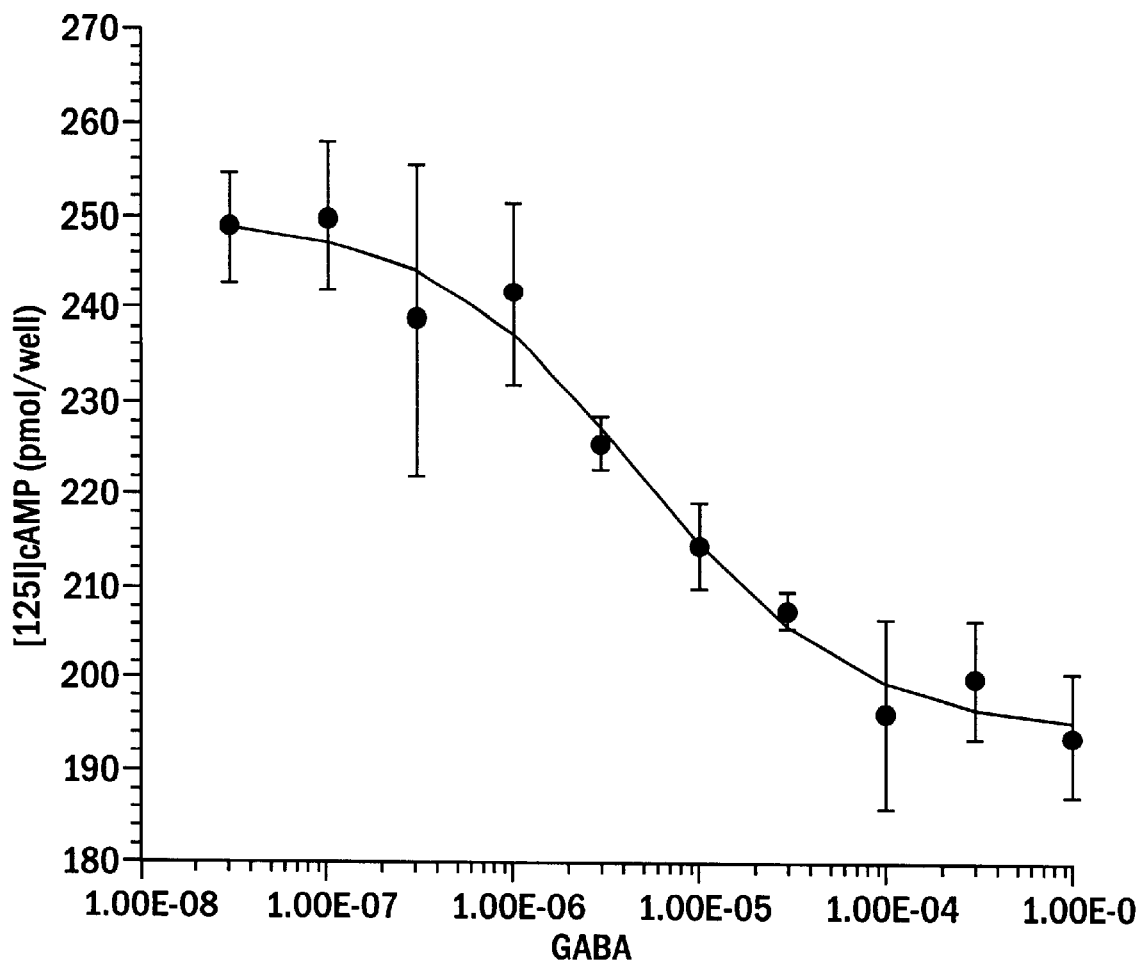

FIGS. 11A and 11B. Coexpression of GABA$_B$-R1 and GABA$_B$-R2 receptors in HEK293T cells permits GABA-mediated inhibition of forskolin-stimulated adenylate cyclase activity.

cAMP levels were measured in HEK293T cells transfected with 1 µg of G$_{i1}$α together with 1 µg of either GABA$_B$-R1a, GABA$_B$-R1b or HA-GABA$_B$-R2; or with 1 µg each of G$_{i1}$α and HA-GABA$_B$-R2 in combination with 1 µg of either GABA$_B$-R1a or GABA$_B$-R1b, as described in Methods. (A) cAMP levels were determined in cells treated with forskolin (50 µM) in the absence (open bars) or presence (hatched bars) of GABA (1 mM). (B) ability of varying concentrations of GABA to inhibit forskolin-elevated adenylate cyclase activity in HEK293T cells expressing G$_{i1}$α and HA-GABA$_B$-R2 in combination with GABA$_B$-R1b. The data shown are the means ±S.D. of triplicate measurements.

FIGS. 12A and 12B. Co-expression of GABA$_B$-R1 and GABA$_B$-R2 receptors in Xenopus oocytes permits agonist-dependant activation of ion flux through CFTR and GIRK1/4.

Xenopus oocytes were injected with cRNA encoding GABA$_B$-R1 and GABA$_B$-R2 receptors (in equal amounts for CFTR, 1:2 ratio for GIRK) plus either CFTR (A) or the GIRK1/GIRK4 heteromer (B). A, Time course plot for an oocyte expressing GABA$_B$-R1, GABA$_B$-R2 and CFTR. Application of 100 mM GABA, 100 mM SKF97541 or 1 mM Baclofen (arrows) activated a large inward CFTR current. Note the increase in CFTR response seen with repeated GABA application. B, Time course plot for an oocyte expressing GABA$_B$-R1, GABA$_B$-R2, GIRK1 and GIRK4. Switching from ND96 (low potassium) to 90K (high potassium) solution led to an inward shift in holding current, showing that the GIRK1/GIRK4 channel is expressed in this oocyte. Subsequent application of 100 mM GABA activated a large inward current (middle panel). Negative and positive control experiments are shown from oocytes expressing the GABA$_B$-R2 receptor alone (left panel) and those expressing the adenosine A1 receptor (right panel).

Figure 13:
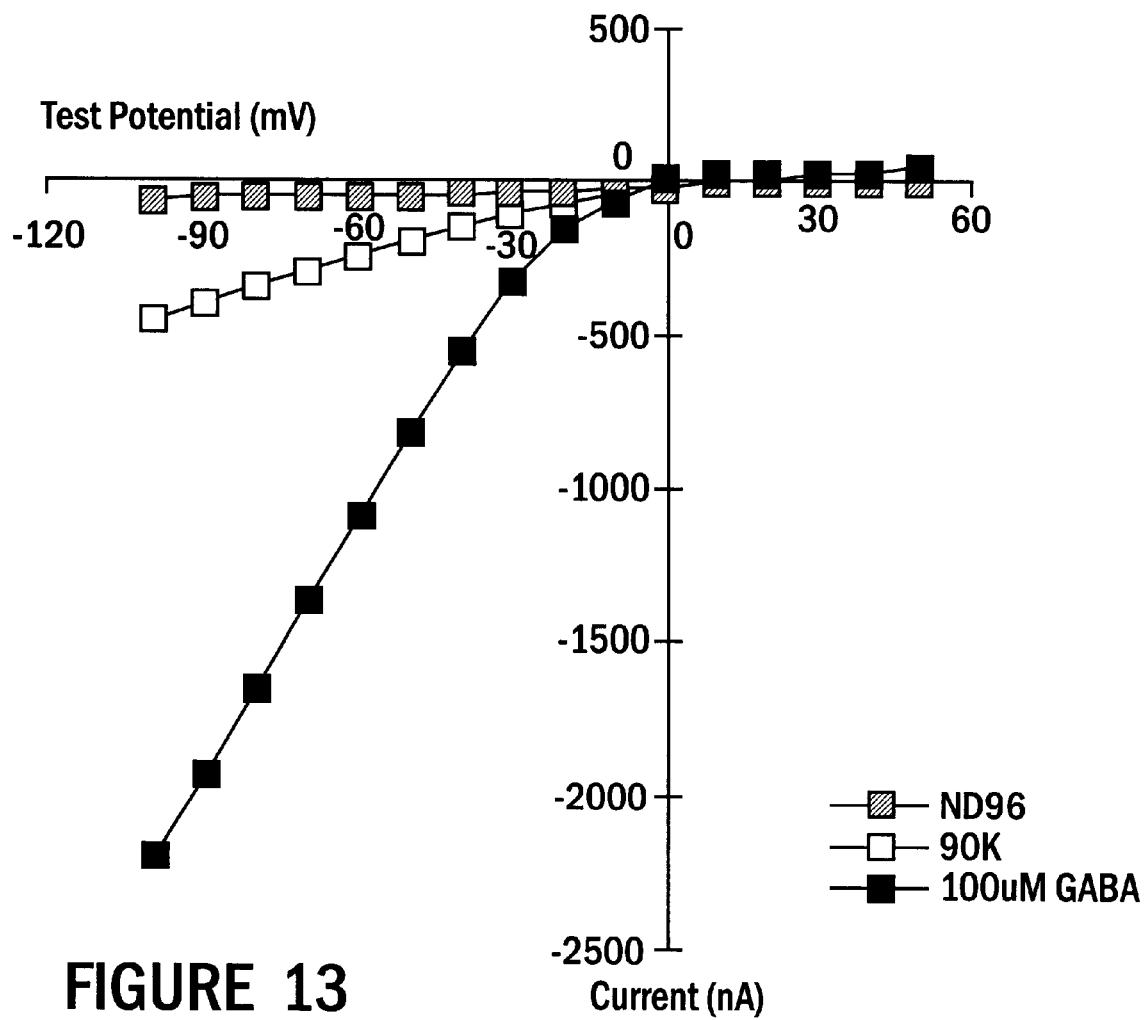

FIG. 13. Current-voltage curves in an oocyte expressing GABA$_B$-R1, GABA$_B$-R2 and the potassium channels GIRK1 and GIRK4.

Current-voltage curves are shown for a single oocyte following application of 200 ms voltage-clamp pulses from a holding potential of −60 mV to test potentials between −100 mV and +50 mV. Steady-state current is plotted against test potential in ND96 solution (low potassium), 90K solution (90 mM potassium) and 90K plus 100 mM GABA. Note the basal GIRK1/4 current recorded in 90K solution and the large agonist-evoked activation of the GIRK potassium channel.

FIG. 14. GABA-mediated stimulation of [$^{35}$S]GTPγS binding activity is dependent on the relative levels of expression of GABA$_B$-R1 and GABA$_B$-R2 receptors.

HEK293T cells were transfected with HA-GABA$_B$-R2 (1 μg) and G$_{o1}$α (1 μg) together with various amounts (0–1 μg) of HA-GABA$_B$-R1b. Cells were harvested 48 h after transfection and P2 membrane fractions were prepared. (A) Agonist stimulation of [$^{35}$S]GTPγS binding activity measured in transfected cell membranes in the presence of GABA (10 mM). Data are shown as stimulation above basal (cpm) and are the mean ±S.D. of triplicate measurements. (B) Cell membranes were immunoblotted with anti-HA antiserum to allow the relative levels of HA-GABA$_B$-R2 and HA-GABA$_B$-R1b receptors to be evaluated.

Figure 15:
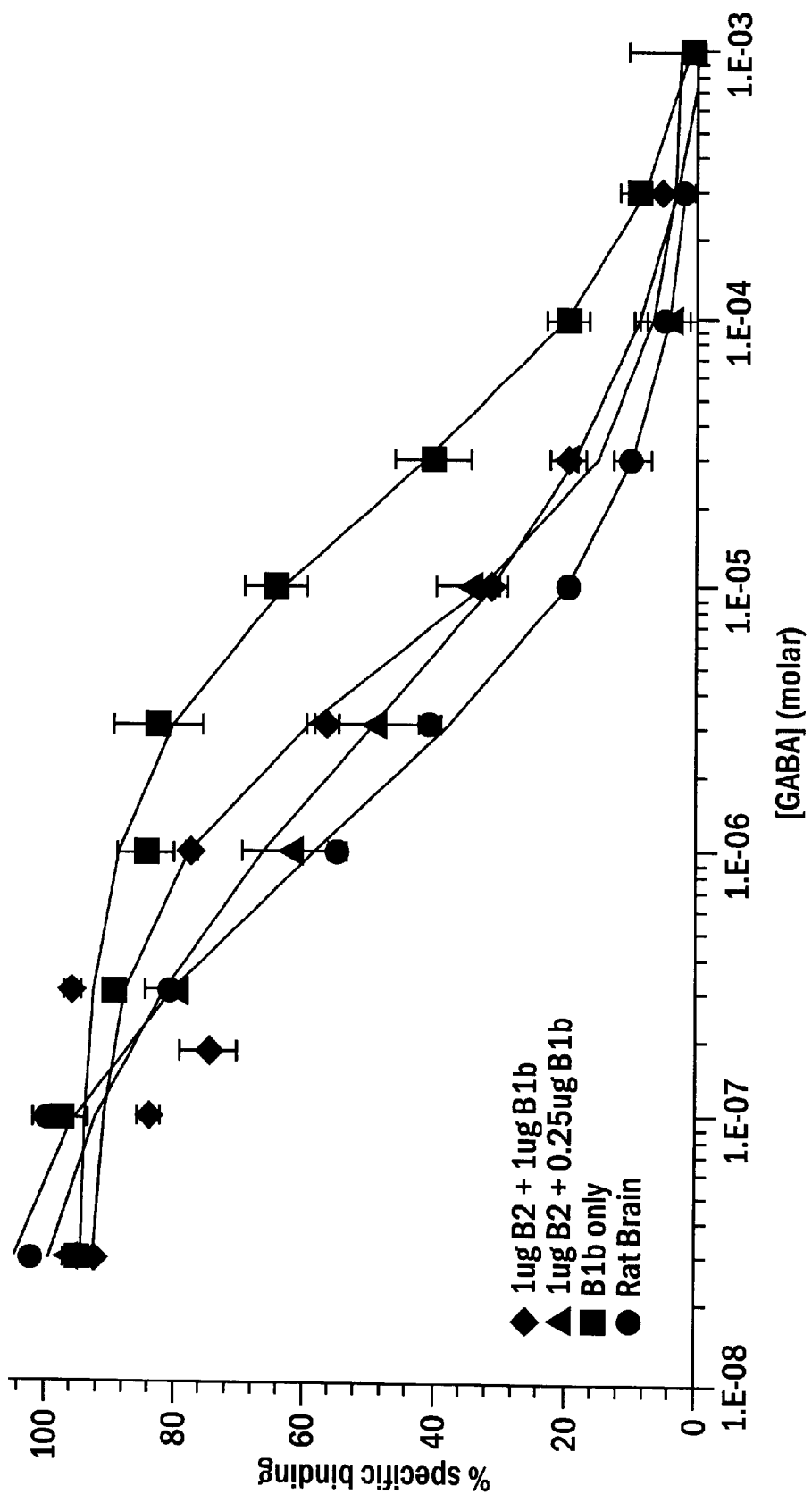

FIG. 15. Co-expression of GABA$_B$-R1 and GABA$_B$-R2 receptors in HEK293T cells generates a high affinity GABA$_B$ binding site similar to brain GABA$_B$ receptors.

P2 membrane fractions were prepared from HEK 293T cells transfected using the same conditions described for GTPγS binding studies. % specific binding was determined for the displacement of [3H]-CGP54626 by GABA. Data shown are the mean of minimum of triplicate studies ±sem.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

As previously explained, the present invention includes a number of important aspects. In particular the present invention relates to isolated GABA$_B$-R2 receptor proteins and variants thereof, isolated GABA$_B$-R1c receptor proteins and variants thereof, GABA$_B$ receptors comprising an heterodimer between a GABA$_B$-R1 receptor protein or a variant thereof and a GABA$_B$-R2 receptor protein or a variant thereof, as well as other related aspects. In the context of the present invention the wording "isolated" is intended to convey that the receptor protein is not in its native state, insofar as it has been purified at least to some extent or has been synthetically produced, for example by recombinant methods. The term "isolated" therefore includes the possibility of the receptor protein being in combination with other biological or non-biological material, such as cells, suspensions of cells or cell fragments, proteins, peptides, organic or inorganic solvents, or other materials where appropriate, but excludes the situation where the receptor protein is in a state as found in nature.

Routine methods, as further explained in the subsequent experimental section, can be employed to purify and/or synthesise the receptor proteins according to the invention. Such methods are well understood by persons skilled in the art, and include techniques such as those disclosed in Sambrook, J. et al, 1989, the disclosure of which is included herein in its entirety by way of reference.

The present invention not only includes the GABA$_B$ receptor proteins specifically recited, but also variants thereof. By the term "variant" what is meant throughout the specification and claims is that other peptides or proteins which retain the same essential character of the receptor proteins for which sequence information is provided, are also intended to be included within the scope of the invention. For example, other peptides or proteins with greater than about 80%, preferably at least 90% and particularly preferably at least 95% homology with the sequences provided are considered as variants of the receptor proteins. Such variants may include the deletion, modification or addition of single amino acids or groups of amino acids within the protein sequence, as long as the biological functionality of the peptide is not adversely affected.

The invention also includes nucleotide sequences which encode for GABA$_B$-R2 or GABA$_B$-R1c receptors or variants thereof as well as nucleotide sequences which are complementary thereto. Preferably the nucleotide sequence is a DNA sequence and most preferably, a cDNA sequence.

The present invention also includes expression vectors which comprise nucleotide sequences encoding for the GABA$_B$-R2 or GABA$_B$-R1c receptor subtypes or variants thereof. A further aspect of the invention relates to an expression vector comprising nucleotide sequences encoding for a GABA$_B$-R1 receptor protein and a GABA$_B$-R2 receptor protein or variants thereof. Such expression vectors are routinely constructed in the art of molecular biology and may involve the use of plasmid DNA and appropriate initiators, promoters, enhancers and other elements, which may be necessary, and which are positioned in the correct orientation, in order to allow for protein expression.

The invention also includes cell lines which have been modified to express the novel receptor. Such cell lines include transient, or preferably stable higher eukaryotic cell lines, such as mammalian cells or insect cells, lower eukaryotic cells, such as yeast or prokaryotic cells such as bacterial cells. Particular examples of cells which have been modified by insertion of vectors encoding for the receptor proteins according to the invention include HEK293T cells and oocytes. Preferably the cell line selected will be one which is not only stable, but also allows for mature glycosylation and cell surface expression of the inventive receptors. In the case of the functional GABA$_B$ receptor which comprises a heterodimer of GABA$_B$-R1 and GABA$_B$-R2 subunits, the cell line may include a single vector which allows for expression of both of the receptor subtypes, or alternatively separate vectors for each subunit. It is preferred however, that the receptor subtypes should be co-expressed in order to optimise the dimerisation process, which will result in full glycosylation and transport of the glycosylated dimer to the cell surface.

It is also possible for the receptors of the invention to be transiently expressed in a cell line or on a membrane, such as for example in a baculovirus expression system. Such systems, which are adapted to express the receptors according to the invention, are also included within the scope of the present invention.

A particularly preferred aspect of the invention is the heterodimer formed between the GABA$_B$-R1 and GABA$_B$-R2 receptor proteins which results in the formation of a functional GABA$_B$ receptor. Without wishing to be bound by theory, it appears that the formation of the heterodimer takes place via the coiled-coil domains within the receptor C-terminal tails, and that this in turn is a pre-requisite for transport and full glycosylation of a GABA$_B$-R1, and also for generation of an high affinity GABA$_B$ receptor at the cell surface.

The heterodimer which forms a functional GABA$_B$ receptor can comprise any GABA$_B$-R1 receptor subtype or splice variant, or variants thereof. Although we are presently only aware of only one GABA$_B$-R2 subtype, it is envisaged that the heterodimers according to the present invention can include other GABA$_B$-R2 subtypes or splice variants which have not yet been identified, as well as variants of the already identified GABA$_B$-R2 receptor proteins.

In particular, the functional GABA$_B$ receptor may include GABA$_B$-R1 receptor proteins selected from GABA$_B$-R1a, GABA$_B$-R1b, GABA$_B$-R1c splice variants, variants thereof or even other GABA$_B$-R1 receptor subtypes or splice variants which have not yet been identified.

According to another aspect, the present invention also relates to antibodies which have been raised by standard techniques and are specific for the receptor proteins or variants thereof according to the invention. Such antibodies could for example, be useful in purification, isolation or screening involving immuno precipitation techniques and may be used as tools to further ellucidate GABA$_B$ receptor function, or indeed as therapeutic agents in their own right. Antibodies may also be raised against specific epitopes of the receptors according to the invention, as opposed to the monomer subunits.

An important aspect of the present invention is the use of receptor proteins according to the invention, particularly the heterodimer GABA$_B$ receptor, in screening methods designed to identify compounds which act as receptor ligands and which may be useful to modulate receptor activity. In general terms, such screening methods will involve contacting the receptor protein concerned, preferably the heterodimeric GABA$_B$ receptor, with a test compound and then detecting modulation in the receptor activity, or indeed detecting receptor inactivity, which results. The present invention also includes within its scope those compounds which are identified as possessing useful GABA$_B$ receptor modulation activity, by the screening methods referred to above. The screening methods comprehended by the invention are generally well known to persons skilled in the art, and are further discussed in the experimental section which follows.

Another aspect of the present invention is the use of compounds which have been identified by screening techniques referred to above in the treatment or prophylaxis of disorders which are responsive to modulation of a GABA$_B$ receptor activity, in a mammal. By the term "modulation" what is meant is that there will be either agonism or antagonism at the receptor site which results from ligand binding of the compound at the receptor. GABA$_B$ receptors have been implicated in disorders of the central nervous system (CNS), gastrointestinal (GI) tract, lungs and bladder and therefore modulation of GABA$_B$ receptor activity in these tissues will result in a positive therapeutic outcome in relation to such disorders. In particular, the compounds which will be identified using the screening techniques according to the invention will have utility for treatment and/or prophylaxis of disorders such as spasticity, epilepsy, Alzheimer's disease, pain as well as affective disorders and feeding disorders. It is to be understood however, that the mention of such disorders is by way of example only, and is not intended to be limiting on the scope of the invention.

The compounds which are identified according to the screening methods outlined above may be formulated with standard pharmaceutically acceptable carriers and/or excipients as is routine in the pharmaceutical art, and as fully described in Remmington's Pharmaceutical Sciences, Mack Publishing Company, Eastern Pennsylvania, 17th Ed, 1985, the disclosure of which is included herein in its entirety by way of reference.

The compounds may be administered via enteral or parenteral routes such as via oral, buccal, anal, pulmonary, intravenous, intraarterial, intramuscular, intraperitoneal, topical or other appropriate administration routes.

Other aspects of the present invention will be further explained, by way of example, in the appended experimental section.

EXPERIMENTAL

Results

1. Cloning of Human GABA$_B$-R1 and a novel Receptor subtype, GABA$_B$-R2

Human homologues to the rat GABA$_B$-R1a and 1b splice variants were identified from ESTs and subcloned from Human cerebellum cDNA, using a combination of PCR and Rapid amplification of cDNA ends (RACE) PCR. Human GABA$_B$-R1a and 1b sequences reveal over 99% identity to the rat GABA$_B$-R1a and GABA$_B$-R1b (data not shown). These receptors, like their rat counterparts, both have signal sequences, followed by extended N-termini, a typical seven-transmembrane topology and short intracellular C-terminal tail. The N-terminus encodes the GABA binding domain, which is predicted by limited homology to bacterial periplasmic proteins to exist as two globular domains that capture GABA (Bettler et al., 1998), as well as three potential N-glycosylation sites. Interestingly the GABA$_B$-R1a splice variant N-terminus encodes 129 amino acids over that of GABA$_B$-R1b, which encode two tandem copies of the 'short consensus repeat' or sushi domain. Sushi domains are approximately 60 amino acids in length and exist in a wide range of proteins involved in complement and cell-cell adhesion (Chou and Heinrikson, 1997). Therefore the sushi domains within GABA$_B$-R1a may direct protein-protein interactions, possibly through cell-cell contact and may reflect a further role for GABA$_B$-R1a, over and above that of GABA$_B$-R1b. Interestingly during the isolation of these clones, a novel N-terminal splice variant, GABA$_B$-R1c was identified. GABA$_B$-R1c differs from GABA$_B$-R1a by a 185bp deletion from bases 290 to 475 (see FIG. 2). This region encodes one of the two Sushi domains unique to GABA$_B$-R1a and therefore the GABA$_B$-R1a and GABA$_B$-R1c splice variants, together with their cellular localisation, may be significant in the biology of GABA$_B$ receptors. Indeed, in situ hybridisations suggest that GABA$_B$-R1a and GABA$_B$-R1b have different sub-cellular localisations, with GABA$_B$-R1a expressed at pre-synaptic rather than at post-synaptic sites (Bettler et al., 1998).

Database searches also identified a number of ESTs showing weaker homology to GABA$_B$-R1, suggesting the existence of a novel GABA$_B$ receptor subtype. Using PCR on Human Brain cerebellum cDNA, we confirmed the existence of such a novel GABA$_B$ receptor which we cloned and sequenced (FIG. 1). This novel receptor, which we have called GABA$_B$-R2, shows an overall 54% similarity and 35% identity to GABA$_B$-R1 over the full length of the protein (FIG. 2). As expected, hydrophobicity profiles for GABA$_B$-R2 (FIG. 3) suggested that the protein has a 42 amino acid signal peptide followed by an extracellular N-terminal domain comparable in size to that of GABA$_B$-R1b and seven membrane spanning regions. In total five N-glycosylation sites were predicted over the N-terminal domain, three of which are conserved within GABA$_B$-R1. Finally, the receptor encodes an intracellular C-terminal domain, which is considerably larger than that of GABA$_B$-

R1. No sushi domains were identified within GABA$_B$-R2 sequence and we have no evidence for any splice variants to date.

2. Tissue Distribution

Expression levels of both GABA$_B$-R1 and GABA$_B$-R2 were determined and compared in different tissues and developmental stages by probing Human RNA Master Blots (Clontech). These blots contain polyA$^+$ RNA samples from 50 human tissues that have been normalized to the mRNA expression levels of eight different "housekeeping" genes. GABA$_B$-R1 levels were examined using a pan-specific probe covering all splice variants (FIG. 4a) and the blots indicate that in accordance with the observations of Kaupmann et al., (1997), GABA$_B$-R1 is highly expressed in the CNS, in all areas of the brain and spinal cord. However, in contrast to Kaupmann et al., (1997), we find that GABA$_B$-R1 is also expressed at comparable levels in peripheral tissues, with particularly high levels of expression in the pituitary, lung, ovary, kidney, small intestine, and spleen. In marked contrast, GABA$_B$-R2 is specifically expressed at high levels only in the CNS, with the possible exception of spinal cord where expression appears somewhat lower. No signal is seen for peripheral tissues, in either adult or fetal tissues (FIG. 4b). This markedly different distribution of mRNA levels between GABA$_B$-R1 and GABA$_B$-R2 suggests that the two subtypes may have distinct roles in the CNS and periphery.

3. Initial Expression Studies

We reasoned that GABA$_B$-R2 could be a high affinity GABA$_B$ receptor and therefore, expressed the receptor in both Xenopus oocytes and HEK293T cells and looked for functional responses. However, despite repeated attempts, we were unable to detect any functional activation of GABA$_B$-R2 or indeed, GABA$_B$-R1a, GABA$_B$-R1b or GABA$_B$-R1c receptors by either GABA itself or GABA$_B$ selective agonists (See FIGS. 9, 11 and 12). Several lines of evidence clearly indicated that GABA$_B$-R1 was not expressed as predicted in vivo. Firstly, flow cytometry of HEK293T cells, expressing GABA$_B$-R1b, revealed that receptors were retained on internal membranes rather than expressed at the cell surface (FIG. 7). Secondly, GABA$_B$-R1a and GABA$_B$-R1b were expressed as immature glycoproteins, by virtue of their sensitivity to endoglycosidases F and H (FIG. 8, lanes 1–6) and finally, GABA$_B$-R1 co-expression in oocytes with either GIRK or CFTR, gave no indication of a functional response (data not shown). We concluded that some additional co-factor must be required to promote a functional response.

4. Yeast Two Hybrid Library Screening

The calcitonin-receptor like receptor is retained as an immature glycoprotein within the endoplasmic reticulum and requires an accessory protein from the recently identified RAMP protein family to transport the receptor to the surface to generate a functional CGRP (Calcitonin generelated peptide) or adrenomedullin receptor (McLatchie et al., 1998). We anticipated that GABA$_B$-R1 receptors should require an analogous trafficking factor or some other protein co-factor for its transport to the cell surface to generate a high affinity receptor. To identify such potential interacting proteins, a yeast two hybrid library screen was run using the C-terminal 108 amino acids of GABA$_B$-R1 against a Human Brain cDNA library. Interestingly, motif searches revealed a strong coiled-coil domain within these 108 residues, a structure known to mediate protein-protein interactions (Lupas, 1996). From a total of 4.3×10$^6$ cDNAs, 122 positives hits were recovered, 33 of which encoded the whole C-terminal domain of GABA$_B$-R2. This domain of the GABA$_B$-R2 is likewise predicted to contain a coiled-coil motif, which aligns exactly with that of GABA$_B$-R1 (see FIG. 2). This observation strongly suggests that the two receptors interact via their C-termini to form a heterodimer. Significantly, the screen did not retrieve the C-terminal domain of the GABA$_B$-R1 itself, implying that GABA$_B$-R1 is unable to homodimerise. This interaction was tested directly in the yeast two hybrid system using the C-termini of the two receptors (FIG. 5). GABA$_B$-R1 and GABA$_B$-R2 were able to strongly interact via their C-termini, whilst neither receptor was able to homodimerise. This observation suggested that GABA$_B$-R1 and GABA$_B$-R2 form heterodimers via their C-terminal coiled-coil domains and led to speculation that homodimerisation may bring about a functional binding site in vivo. Therefore, we next confirmed the interaction between the two receptor subtypes by immunoprecipitation studies upon whole epitope-tagged receptor in transfected HEK293T cells.

5. Co-immunoprecipitation Studies

Epitope tagged receptors, Myc-GABA$_B$-R1b and HA-GABA$_B$-R2 were transiently expressed in HEK293T cells either alone or in combination. Immunoprecipitation of Myc-GABA$_B$-R1b from detergent-solubilised cell fractions with Myc antisera led to immunodetection of HA-GABA$_B$-R2 within immune complexes using HA as the primary antibody, but only upon receptor co-expression (FIG. 6, lanes 1–3). GABA$_B$-R1 and GABA$_B$-R2 association was confirmed by co-immunodetection of Myc-GABA$_B$-R1b from immune complexes captured using the anti-HA antibody. Once again, co-immunoprecipitation could only be seen when the two receptor forms were co-expressed (FIG. 6, lanes 4–6). Hence in agreement with the yeast two hybrid observations, these data provide compelling evidence for heterodimerisation between full-length expressed GABA$_B$-R1 and GABA$_B$-R2 in mammalian cells. Therefore, we next examined GABA$_B$ receptor responses following co-expression of both receptor subtypes in HEK293T cells or in Xenopus oocytes.

6. Surface Expression of the Heterodimer

HEK293T cells were transiently transfected with Myc-GABA$_B$-R1b alone or in combination with HA-GABA$_B$-R2 and transfectants analysed by flow cytometry (FIG. 7). Myc-immunoreactivity could not be detected on the surface of cells transfected with Myc-GABA$_B$-R1b alone (FIG. 7a), although cell permeabilisation revealed immunoreactivity in 35% (n=3) of the cell population (FIG. 7b). This latter observation indicated that cells were efficiently transfected and suggested that expressed Myc-GABA$_B$-R1 receptors were localised exclusively on internal membranes. In contrast, 14% (n=3) of HEK293T cells transfected with HA-GABA$_B$-R2 showed surface immunoreactivity (FIG. 7c). However, co-transfection of both Myc-GABA$_B$-R1b and HA-GABA$_B$-R2 led to the appearance of Myc-GABA$_B$-R1b on the surface of 20% (n=3) of cells analysed (FIG. 7a), strongly suggesting that co-expression of GABA$_B$-R1b with GABA$_B$-R2 is necessary for surface expression of GABA$_B$-R1b.

7. Receptor Glycosylation Studies

Endoglycosidases F and H can be used to differentiate between core and terminally glycosylated N-linked glycoproteins. Therefore, these enzymes were used to examine the glycosylation status of both GABA$_B$-R1 and GABA$_B$-R2 following expression in HEK293T cells. Membranes from transfected cells were treated with either endoglycosidase F or endoglycosidase H and expressed GABA$_B$ receptors were characterised by immunoblotting to compare relative electrophoretic mobilities of the receptors (FIG. 8). Cell membranes expressing either GABA$_B$-R1a or 1b produced distinct bands of M$_r$ 130 and 100K respectively (FIG. 8, lanes 1 and 4) which following endoglycosidase F treatment, decreased in size to single immunoreactive species of M$_r$ 110 and 80K; representing GABA$_B$-R1a and GABA$_B$-R1b respectively (FIG. 8, lanes 2 and 5). This shows that recombinant GABA$_B$-R1a and 1b are glycoproteins, in agreement with the observations of Kaupmann et al., (1997). However, both GABA$_B$-R1a and 1b splice variant forms were also sensitive to endoglycosidase H treatment, indicating that the expressed proteins are only core glycosylated (lanes 3 and 6) and lack terminal glycosylation. This observation, together with the FACS analysis, suggests that the proteins are immaturely glycosylated and retained on internal membranes. Significantly, when either GABA$_B$-R1a (lanes 7–9) or GABA$_B$-R1b (lanes 10–12) was co-expressed with HA-GABA$_B$-R2, a component of GABA$_B$-R1a or 1b was resistant to endoglycosidase H digestion suggesting that when co-expressed with GABA$_B$-R2, a significant fraction of GABA$_B$-R1 is now a mature glycoprotein (lanes 9 and 12).

Similar studies with HA-GABA$_B$-R2 gave an immunoreactive species with an M$_r$ of 120 K (FIG. 8, lanes 13, 16, 19) which was sensitive to endoglycosidase F (lanes 14, 17 and 20) but resistant to endoglycosidase H (lanes 15, 18 and 21) treatment, whether expressed alone or in combination with GABA$_B$-R1. Thus, these data indicate that expressed HA-GABA$_B$-R2 is a mature glycoprotein whose glycosylation status is not affected by co-expression with GABA$_B$-R1. Thus, heterodimerisation between GABA$_B$-R1 and GABA$_B$-R2, possibly in the Golgi complex, could be a prerequisite for maturation and transport of GABA$_B$-R1 to the plasma membrane.

8. Functional Studies

To determine whether co-expression of GABA$_B$-R1 and GABA$_B$-R2 and its subsequent mature glycosylation and cell surface expression, generated a receptor complex able to functionally respond to GABA, we measured three types of signalling. We used transiently transfected HEK239T cells to examine firstly, activation of [$^{35}$S]GTPγS binding in membranes and secondly, inhibition of forskolin stimulated cAMP activation in whole cells. Thirdly we expressed GABA$_B$-R1 and GABA$_B$-R2 in Xenopus oocytes, expressing either the cystic fibrosis transmembrane regulator (CFTR) or inwardly rectifying K$^+$ channels (GIRK and KATP) and examined activation of ion flux in response to agonist.

i. [$^{35}$S]GTPγS Binding

No GABA stimulated [$^{35}$S]GTPγS binding was observed in membranes prepared from cells transfected with either GABA$_B$-R1 or HA-GABA$_B$-R2 in combination with G$_{o1}$α. However, co-expression of GABA$_B$-R1 and HA-GABA$_B$-R2 together with G$_{o1}$α resulted in a robust stimulation of [$^{35}$S]GTPγS binding activity (FIG. 9a). This was found to be concentration-dependent with similar EC$_{50}$ (mean, ±S.E.M., n=3) values determined for membranes from cells transfected with HA-GABA$_B$-R2 and G$_{o1}$α together with either GABA$_B$-R1a (9.5±1.1×10$^{-5}$M) or GABA$_B$-R1b (7.8±0.4×10$^{-5}$M) (FIG. 9b). These values are equivalent to those of GABA-mediated stimulation of [$^{35}$S]GTPγS binding to rat brain membranes (5.9±0.4×10$^{-5}$M) (data not shown). We were concerned that an N-terminal HA epitope tag on GABA$_B$-R2 could alter receptor function and so we performed parallel studies in HEK293T cells, expressing untagged versions of GABA$_B$-R2 and GABA$_B$-R1 together with G$_{o1}$α. Similar efficacies and potencies of GABA action were observed in membranes from these cells, as reported for the epitope tagged receptors (data not shown), clearly suggesting that the addition of these peptide sequences to the N-termini of GABA$_B$-R2 and GABA$_B$-R1 did not significantly alter receptor function. It is noteworthy that a measurable GABA-mediated elevation of [$^{35}$S]GTPγS binding activity was only observed upon co-expression of GABA$_B$-R1 and HA-GABA$_B$-R2 together with additional G$_{o1}$α (FIG. 10). The requirement for additional G protein is most likely due to relatively low levels of endogenously expressed G$_{i/o}$ family G proteins, thus precluding a discernible GABA-mediated response upon GABA$_B$-R1 and GABA$_B$-R2 co-expression.

ii cAMP Inhibition

Similar results were obtained from HEK293T cells transiently transfected with GABA$_B$-R1 and GABA$_B$-R2, using inhibition of forskolin evoked cAMP as a readout. Once again, functional responses were only observed when both GABA$_B$-R1 and GABA$_B$-R2 were co-expressed (FIG. 11).

iii Xenopus Oocytes

Xenopus oocytes can assay for three classes of G-protein:
1) Endogenous oocyte Ca$^{2+}$-activated chloride conductance can assay for activation of G$_q$ and a subsequent rise in intracellular calcium (Uezono et al., 1993).
2) Cystic fibrosis transmembrane regulator (CFTR), which contains a cAMP-activated chloride channel, can assay for receptor activation via G$_s$ or G$_{i/o}$ (Uezono et al., 1993; Wotta et al.,1997).
3) G-protein regulated potassium channels GIRK1 (Kir 3.1; Kubo et al., 1993) and GIRK4 (or CIR, Kir 3.4, Kaprivinsky et al., 1995), injected in equal amounts to generate a heteromeric channel, can assay for activation of pertussis toxin sensitive G-proteins (Kovoor et al., 1997).

No functional responses to GABA or baclofen were seen when cloned GABA$_B$-R1a, GABA$_B$-R1b or GABA$_B$-R2 receptors were expressed in oocytes in combination with CFTR or GIRK1/4 (data not shown; see FIG. 12b). When GABA$_B$-R1 and GABA$_B$-R2 were co-expressed with CFTR, several significant, robust responses were recorded following application of 100 μM GABA (FIG. 12a). Moreover, repeated application of GABA led to a progressive increase in the size of the CFTR response, suggesting that the functional response of the heterodimer is now sensitised to further challenge by agonist. This phenomenon has not been observed for other cloned receptors expressed in oocytes and may be related to the heterodimerisation or even oligomerisation of the GABA$_B$ receptors. Finally, two other GABA$_B$-selective agonists, Baclofen and SKF97541 elicted similar functional responses through CFTR to that of GABA (FIG. 12a). In contrast, antagonists gave no response (data not shown).

Next, we examined the GABA$_B$-R1/GABA$_B$-R2 heterodimer with the G-protein regulated potassium channels GIRK1 and GIRK4 and once again found agonist dependent responses. Time course plots were examined for three individual oocytes expressing GABA$_B$-R2 alone (left panel), GABA$_B$-R1 plus GABA$_B$-R2 (middle panel) and the adenosine A1 receptor (as a positive control, right panel) (FIG. 12b). In each case, switching from a low potassium physiological solution (ND96) to a high potassium extracellular solution (90 mM K$^+$) led to an inward shift in holding current, resulting from agonist-independent influx of potassium ions through the GIRK1/4 channel. No GABA response was seen in oocytes expressing GABA$_G$-R2 in isolation (FIG. 12b, left panel) and similarly, GABA$_B$-R1a and GABA$_B$-R1b expressed alone also gave no response to GABA (data not shown). Significantly, a large GABA response was recorded in oocytes co-expressing GABA$_B$-R1 and GABA$_6$-R2 (FIG. 12b, middle panel) of a similar magnitude to that of the adenosine A1 receptor in response to the agonist NECA (FIG. 12b, right panel). Thus, once again co-expression of the two receptor subtypes elicits a functional agonist-dependant response, whereas expression of either subtype receptor alone does not. We also examined whether co-expression of the two receptors in oocytes could activate endogenous Ca$^{2+}$-activated chloride conductance. No evidence for activation was seen (data not shown) suggesting that at least in oocytes, the GABA$_B$-R1/GABA$_B$-R2 receptor complex does not signal through G$_q$. Finally, a current-voltage curve were constructed for an oocyte co-expressing GABA$_B$-R1 and GABA$_B$-R2 (FIG. 13). This clearly demonstrates that GABA, bound to the GABA$_B$ receptor, activates a large inwardly rectifying current consistent with activation of the GIRK potassium channel in a fully dose dependant manner.

9. Stoichiometric Studies on the Heterodimer

Since co-expression of GABA$_B$-R1 and GABA$_B$-R2 is necessary for a functional GABA$_B$ receptor, we decided to investigate stoichiometric ratio between the two receptor subtypes in vivo. Relative levels of expression for both GABA$_B$-R1 and GABA$_B$-R2 were measured following transfection into HEK293T cells and compared to receptor function, as determined by GTPγS binding (FIG. 14). Increasing amounts of HA-GABA$_B$-R1 (up to 1 μg) plasmid were transfected into HEK293T cells along with a constant (1 μg) amount of HA-GABA$_B$-R2. GABA caused stimulation of [$^{35}$S]GTPγS binding above basal levels in membranes extracted from these cells, which increased with increasing amount of transfected HA-GABA$_B$-R1 until binding reached a plateau when levels of HA-GABA$_B$-R1 were greater than 0.25 μg (FIG. 14a). Immunoblotting of the same membrane samples revealed equivalent levels of expression of HA-GABA$_B$-R1 and HA-GABA$_B$-R2 in membranes transfected with 0.25–0.5 μg of HA-GABA$_B$-R1 (FIG. 14b). This corresponded to the plateau of GABA-mediated elevation of [$^{35}$S]GTPγS binding activity and therefore strongly suggests that GABA$_B$-R1 and GABA$_B$-R2 functionally interact in a 1:1 stoichiometric ratio.

10. Competition Binding Studies

Finally, we determined whether the observed functional responses were due to a high affinity GABA$_B$ receptor, composed of a heterodimer of the two receptors. HEK293T cells were transfected with either 1 μg HA-GABA$_B$-R1b and HA-GABA$_B$-R2 individually or with increasing amounts (up to 1 μg) of HA-GABA$_B$-R1b and a fixed amount (1 μg) of HA-GABA$_B$-R2 together with G$_{o1}$α. Competition binding assays were then performed upon purified membranes. Expression of HA-GABA$_B$-R1b alone produced high levels of specific binding of [$^{35}$H]-CGP54626 (Bittiger et al., 1992), a structural analogue of [$^{125}$I]-CGP64213 and the antagonist originally used to expression clone GABA$_B$-R1 (Kaupmann et al., 1997). However, as previously reported for [$^{125}$I]-CGP64213, GABA inhibition curves were significantly shifted to the right compared with binding to rat brain membranes (FIG. 15), giving approximately 22-fold lower IC$_{50}$ than rat brain binding. Significantly, co-expression of equivalent amounts of HA-GABA$_B$-R1b and HA-GABA$_B$-R2 protein revealed high levels of specific binding. In a control experiment using untagged receptors similar values were obtained (data not shown). Achievement of a 1:1 stoichiometric ratio of expression of HA-GABA$_B$-R1b and HA-GABA$_B$-R2 led to agonist inhibition curves similar to those obtained in rat brain membranes (IC$_{50}$±95% confidence intervals for 1 μg HA-GABA$_B$-R2/0.25 μg HA-GABA$_B$-R1b=2.29 μM (1.48–3.55 μM) and for rat brain=1.04 μM (0.69–1.58 μM). Such comparable levels of receptor expression were also shown to permit optimal agonist activation in the GTPγS assay (see FIG. 14). Alteration of receptor ratio from 1:1, such that GABA$_B$-R1b was the most prevalent receptor, led to reduced agonist affinity, presumably due to binding at non-dimerised and immaturely glycosylated GABA$_B$-R1b receptors (FIG. 15).

In addition, despite its apparent cell surface expression, we were unable to detect any [3H]-CGP54626 specific binding to HEK293T cells transiently transfected with HA-GABA$_B$-R2 alone (data not shown). We conclude that heterodimerisation of the GABA$_B$-R1 and GABA$_B$-R2 subtypes are necessary to generate a high affinity GABA$_B$ receptor. There are a number of possible explanations for the change in GABA affinity following co-expression of the two receptor subtypes. Appearance of the GABA$_B$ receptor complex at the cell surface would be expected to allow G protein coupling of the receptor which would increase agonist affinity. However, in previous studies is has been shown that the lack of G protein coupling alone cannot account for the difference in agonist affinity between rat brain receptors and GABA$_B$-R1 (Kaupmann et al., 1997). Furthermore, we have noted that [$^3$H]-CGP54626 appears to primarily bind the low affinity state of the receptor, even in rat brain membranes, as demonstrated by the fact that GTPγS is unable to shift agonist inhibition curves and actually increases the level of $^3$H-CGP54626 specific binding (data not shown). Therefore, a more likely explanation for the change in GABA affinity following co-expression of the two GABA$_B$ receptors is that heterodimerisation together with the mature glycosylation state of the protein, produces a binding site conformation with an inherent higher affinity.

Discussion

Functional GABA$_B$ receptors within the CNS comprise a cell surface heterodimer of two distinct 7-transmembrane receptor subunits, GABA$_B$-R1 and GABA$_B$-R2 in a 1:1 stoichiometric ratio. In vivo, GABA$_B$ receptors may exist simply as heterodimers or form even larger multimeric complexes of many heterodimers. Formation of the heterodimer via the coiled-coil domains within the receptor C-terminal tails appears to be a pre-requisite for transport and full glycosylation of GABA$_B$-R1, as well as for the generation of a high affinity GABA$_B$ receptor at the cell surface. Using this information, we have been able to reproduce GABA$_B$ sites in both mammalian HEK293T cells as well as in oocytes, using several functional readouts such as activation of ion flux through CFTR or GIRK in oocytes, or inhibition of adenylyl cyclase in HEK293T cells. Indeed the lack of functional responses in cells expressing GABA$_B$-R1 alone and the need for expression of a second 7TM receptor explains why many groups have encountered extreme difficulty in expression cloning a GABA$_B$ receptor via conventional means. We believe this is the first report of receptor heterodimerisation as an obligate requirement to generate a high affinity, fully functional receptor in recombinant systems, which is fully equivalent to that of endogenous tissues.

Dimerisation has been reported for other receptor families, such as the opioid family as a part of their desensitisation process, the β2-adrenergic receptor, where homodimers may play a role in signalling, and the metabotropic glutamate receptors (mGluRs, Hebert et al., 1996; Romano et al., 1996; Cvejic et al., 1997, Hebert and Bouvier, 1998). Significantly, dimerisation in these receptor families does not appear to be an absolute requirement for functional coupling in recombinant systems. In the case of the mGluRs, which are a closely related receptor family to GABA$_B$ (Kaupmann et al., 1997), homodimerisation is mediated through disulphide bridges between the N-terminal extracellular domains rather than a C-terminal coiled-coil. Indeed, heterodimerisation between two 7-transmembrane receptors, leading to both trafficking and mature glycosylation of the proteins to yield a functional receptor is unprecedented and is unique in the GPCR field. Certainly, mGluRs have not been found to form heterodimers (Romano et al., 1996) and the fact that two such closely related receptors families have evolved such different mechanisms of dimer formation suggests that this is a fundamentally important process for receptor function.

In vivo, pharmacological evidence suggests that there are many different GABA$_B$ receptor subtypes, both within the CNS as well as in peripheral tissues. How are such pharmacological subtypes of GABA$_B$ receptors formed? Only GABA$_B$-R1 and GABA$_B$-R2 have been identified as separate genes to date and database trawling has not identified any further receptors homologous to known GABA$_B$ receptors. This does not exclude the possibility that more, as yet unrecognised GABA$_B$ receptors do exist. Differences in distribution exist for the two GABA$_B$ receptors, for example GABA$_B$-R2 is specifically expressed in the CNS whereas GABA$_B$-R1 is expressed in both central and peripheral sites. These differences in distribution clearly add further complexity leading to the pharmacologically distinct receptor subtypes. Moreover, the genes encoding the GABA$_B$ receptors may be differentially spliced. GABA$_B$-R1 encodes three N-terminal splice variants and yet more may remain to be detected. Interestingly, these splice variants have alterations in their N-terminal extracellular domain, the region involved in GABA binding (Takahashi et al., 1993, O'Hara et al., 1993) and encode either two (GABA$_B$-R1a), one (GABA$_B$-R1c) or no (GABA$_B$-R1b) sushi domains. Given that the sushi domains mediate cell-cell protein-protein contact, the differences in these three splice variants may account for yet more of the pharmacologically defined GABA$_B$ receptor subtypes. To date, we have not detected any splice variants to GABA$_B$-R2. Furthermore there are significant differences in the distribution of the individual splice variants suggesting that they may serve different functions within the CNS. For instance, GABA$_B$-R1a splice variant is reported as presynaptic within the brain (Bettler et al., 1998) and therefore may define presynaptic GABA$_B$ autoreceptors. It seems likely that these splice variants of GABA$_B$-R1 may account for at least some of the pharmacologically defined subtypes. Finally, with this novel observation of obligate receptor heterodimerisation, a further level of complexity has been added since functional GABA$_B$ binding sites require a heterodimerisation partner.

Now the molecular nature of the GABA$_B$ receptor is more fully understood, recombinant systems can be established for high throughput screening for compounds against individual pharmacologically defined GABA$_B$ sites. By these means, compounds with greater specificity and with fewer unwanted side effects can be discovered. For this, GABA$_B$-R1 and GABA$_B$-R2 (including all spice variants, and any fragments of the receptor) should be co-expressed either stably or transiently in suitable host cells. Suitable host cells include higher eukaryotic cell lines, such as mammalian cells, insect cells, lower eukaryotic cells, such as yeast or prokaryotic cells such as a bacterial cells. Screening assays with these recombinant cell lines could involve the use of radioligand binding to the dimer or individual subunits within the dimer. The activity profile in a binding assay to the dimer is likely to be different from the activity of compounds assayed using binding assays to GABA$_B$-R1 alone due to alterations in the glycosylation status and the conformation of the receptor as a result of co-expressing GABA$_B$-R1 or GABA$_B$-R2. Functional assays, which measure events downstream of receptor activation, can also be used for screening compounds. Such assays include [$^{35}$S]-GTPγS binding to membranes isolated from cells expressing the dimer; activation or inhibition of ion channels using electrophysiological recording or ion flux assays; mobilisation of intracellular calcium; modulation of cAMP levels; activation or inhibition of MAP kinase pathways or alterations in the activity of transcription factors with the use of reporter genes. Further to this, secondary screens can be established in a similar manner, using different heterodimer combinations to exclude unwanted activity and thereby establish subtype selective GABA$_B$ compounds.

In addition, any approach targetting the disruption or enhancement of dimer formation of the GABA$_B$ heterodimer could represent a novel therapeutic approach with which to target GABA$_B$ receptors. Such strategies could include peptides or proteins physically associated with the coiled-coil domain or indeed, any other interacting regions of the dimer. Small molecules could also be identified which act at the points of contact formed by interaction of the components of the dimer. These may either promote or enhance the receptor function. Finally, antibodies could be made which specifically recognise epitopes on the dimer, as opposed to the monomer subunits. These could be used as tools to further elucidate the function of GABA$_B$ receptors in disease or as therapeutic agents in their own right.

Methods

DNA Manipulation

Standard molecular biology protocols were used throughout (Sambrook et al., 1989) and all bacterial manipulations used Escherichia coli XL-1Blue (Stratagene) according to the manufacturers instructions. Standard PCR conditions were used throughout, unless otherwise stated. PCR reaction mixture contained 10–50 ng of target DNA, 1 pmol of each primer; 200 μM dNTPs and 2.5 U of either Taq polymerase (Perkin-Elmer) or Pful polymerase (Stratagene) with the appropriate buffer as supplied by the manufacturer. Cycling parameters were 1 cycle 95° C. 2 mins; 25 cycles 95° C. 45 secs 55° C. 45 secs 72° C. 1 min; 1 cycle 72° C. 10 mins. All PCR were carried out using either a Perkin Elmer 9600 PCR machine or a Robocycler Gradient 96 (Stratagene) PCR machine.

GABA$_B$-R1—Cloning of Human Homologues and Splice Variants

Several human EST's (X90542; X90543; D80024; AA348199; T06711; T07518 and AA38224) were identified as homologous to the rat GABA$_B$-R1a and GABA$_B$-R1b sequences (Y10369; Y10370). The ESTs were aligned and the predicted open reading frame was amplified by RT-PCR from human brain cerebellum polyA$^+$ RNA (Clontech) using the Superscript Preamplification System (Life Technologies). The 3' end of the receptor (1545–2538 bp; GABA$_B$-R1b) was amplified using primers 5'-GCGACTGCTGTGGGCTGCTTACT GGC-3 (SEQ ID NO:1) and 5'-GCGAATTCCCTGTCCTCCCTCACCCTACCC-3' (SEQ ID NO:2). The central section (277–1737 bp of GABA$_B$-R1b) was amplified using 5'-CCGAGCTCAAGCTCATCCACCACG-3' (SEQ ID NO:3) and 5'-TCTTCCTCCACTCCTTCTTTTCTT-3' (SEQ ID NO:4). PCR products were subcloned into pCR-Script SK(+) (PCR-script Amp cloning kit; Stratagene). Error free PCR product were assembled in a three-way BstEII, SacI and EcoRI ligation and subcloned into pBluescript SK (−) (Stratagene).

The N-termini of the splice variants were generated using RACE (rapid amplification of cDNA ends) PCR with the Marathon cDNA amplification kit against Marathon-Ready human cerebellum cDNA (Clontech). RACE PCR was primed from a conserved sequence within GABA$_B$-R1 using primer 5'-TGAGCTGGAGCCATAGGAAAGCACAAT-3' (SEQ ID NO: 5) to generate a 700 bp product. This further PCR amplified using the AP2 primer (Marathon) and a second internal GABA$_B$-R1 primer 5'-GATCTTGATAGGGTCGTTGTAGAGCA-3'(SEQ ID NO:6). The resulting 600 bp product was subcloned using the Zero blunt PCR cloning kit (Invitrogen). Sequence information achieved from this RACE PCR was used to clone the N-terminus of the GABA$_B$-R1b splice variant, using primers 5'-GCTCCTAACGCTCCCCAACA-3' (SEQ ID NO:7) and 5'-GGCCTGGATCACACTTGCTG-3' (SEQ ID NO:8) into pCR-Script SK (+)(Stratagene). Human GABA$_B$-R1a 5' sequences were retrieved from Incyte database EST's (1005101 ;3289832) and used to design primers 5'-CCCAACGCCACCTCAGAAG-3' (SEQ ID NO:9) and 5'-CCGCTCATGGGAAACAGTG C-3' (SEQ ID NO:10). PCR on cerebellum cDNA and KELLY neuroblastoma cell line cDNA produced two discreet bands at 300 bp and 400 bp, which were cloned into pCR-Script SK (+) (Stratagene). Sequencing revealed that the 400 bp product encoded some of the Human GABA$_B$R1a 5' sequences and the 300 bp product encoded the novel splice variant, GABA$_B$-R1c. Next, primer, 5'-CCCCGGCACACATACTCAATCTCATAG-3' (SEQ ID NO:11) was designed to RACE PCR the missing 225 bp of GABA$_B$-R1a. A 250 bp product was obtained and reamplified using primer 5'-CCGGTACCTGATGCCCCCTTCC-3' (SEQ ID NO:12) with primer AP2 (Marathon). A 250 bp band was once again generated, subcloned into pCR-Script SK (+) and when sequenced, encoded the 5' end of GABA$_B$-R1a. Next, clones spanning both the conserved receptor sequence and the %' ends of the splice variants GABA$_B$-R1a and GABA$_B$-R1c were generated. Primer 5'-CGAGATGTTGCTGCTGCTGCTA-3' (SEQ ID NO:13), priming from the start codon and the reverse RACE primer generated a predicted 800 bp band and this was subcloned into pCR-Script SK(+). Now, full-length GABA$_B$-R1a, GABA$_B$-R1b and GABA$_B$-R1c clones can be assembled in pcDNA3.1(-) (Invitrogen). For GABA$_B$-R1b, 5' sequences, restricted NotI/SacI, and the conserved region of the receptor, cut EcoRI/SacI were both co-ligated into pcDNA3.1(-), restricted NotI/EcoRI. Likewise, the GABA$_B$-R1a and GABA$_B$-R1c 5' fragments were subcloned XhoI/SacI with the EcoRI/SacI conserved fragment and co-ligated into pcDNA3.1(-), cut XhoI/EcoRI to reconstitute full length clones.

Tagging of GABA$_B$-R1b

GABA$_B$-R1b was tagged with either myc or HA epitopes. PCR primers 5'-TAGGATCCCACTCCCCCCATCCC-3' (SEQ ID NO:14) and 5'-CCAGCGTGGAGACAGAGCTG-3' (SEQ ID NO:15) were used to amplify a region immediately following the proposed signal sequence (position 88) to approx. 20 bp downstream of a unique PstI site at position 389 of the coding sequence, creating a unique 5' in-frame BamHI site. This fragment was cloned, BamHI/PstI, into a vector containing the CD97 signal sequence, the myc epitope and an in-frame BamHI site. This construct also contains a NotI site 5' to the CD97 signal sequence and an EcoRI site downstream of the PstI site. GABA$_B$-R1b sequences downstream to the PstI site and upto an external EcoRI site were subcloned from full length receptor into the vector described above likewise cut with PstI/EcoRI, to assemble full length tagged GABA$_B$-R1b. CD97 signal sequence, myc epitope and GABA$_B$-R1b coding sequence were subcloned, NotI/EcoRI, into pCDNA3.1(-) (Invitrogen). HA epitope was added to GABA$_B$-R1b by co-ligation of the 5' BamHI/PstI and 3' PstI/EcoRI fragments into pCIN6 cut with BamHI/EcoRI. This vector contains a T8 signal sequence and 12CA5 HA epitope immediately preceding an in-frame BamHI site.

Cloning of GABA$_B$-R2, the Novel GABA$_B$ Receptor Subtype

EST clones (H14151, R76089, R80651, AA324303, T07621, Z43654) were identified with approximately 50% nucleotide identity to GABA$_B$-R1. PCR revealed that H14151 contained a 1.5 Kb insert and encoded sufficient sequence for a substantial portion the novel GABA$_B$ receptor. PCR between the 3' end of H14151 and the 5' end of AA324303, using a cerebellum cDNA library as template, produced a 700 bp product, which when cloned into the T-vector (TA cloning kit, Invitrogen) and sequenced, revealed that T07621 overlaps within AA324303. Also, Z43654 as well as genomic DNA fragments R76089 and R80651 were found to overlap AA324303 and together provided sequence data for the 3' end of the GABA$_B$ subtype receptor. Further sequencing of H14151 provided the full sequence for the novel receptor subtype. However, because of ambiguities in the position of the stop codon in Z43654/R80448/R80651, Incyte clones 662098 and 090041, which overlap this region, were sequenced. The stop codon was identified and sequence for GABA$_B$-R2 was confirmed as within H14151 (5' end) and 662098 (3' end). 5' sequences of GABA$_B$-R2 were PCR generated using primers 5'-ATGGCTTCCCCGCGGAG-3' (SEQ ID NO:16) to provide the start codon of the receptor and primer 5'-GAACAGGCGTGGTTGCAG-3' (SEQ ID NO:17), priming beyond a unique EagI site. The expected ~250 bp product was cloned into pCRSCRIPT and sequenced. Full length receptor was then assembled with a three way ligation between H14151, cut with ApaLI/EagI; 662098, cut with ApaLI/NotI and pCRSCRIPT-GABA$_B$-R2–5' PCR product, restricted by EagI.Full length GABA$_B$-R2 was removed from the pCRSCRIPT vector using EcoRI/NotI and ligated into pcDNA3 (Invitrogen) for expression studies.

HA-epitope tagged GABA$_B$-R2 was constructed in pCIN6,.A linker was constructed encoding amino acids between the GABA$_B$-R2 signal sequence and the unique EagI site.

```
         HindIII XhoI                                                  EagI    EcoRI
     AGCTT CTC GAG GCT TGG GGA TGG GCA CGA GGA GCT CCT GCT CGG CCG G (SEQ ID NO:18)

A GAG CTC CGA ACC CCT ACC CGT GCT CCT CGT GGT CGA GCC GGC CTT AA (SEQ ID NO:19)

Ala Trp Gly Trp Ala Arg Gly Ala Pro Arg (SEQ ID NO:20)
```

The linker was cloned into pUC18 (EcoRI/HindIII) followed by full length GABAB-R2, from pCRSCRIPT as an EagI/

NotI fragment. Finally, the modified GABA$_B$-R2 was cloned into pCIN6 as a XhoI fragment.

Distribution Studies

Blots were hybridized overnight at 65° C. according to the manufacturers' instructions with radioactively randomly primed cDNA probes using ExpressHyb Hybridization solution. Probe for GABA$_B$-R1, corresponding to residues 1129–1618 of the GABA$_B$-R1b coding sequence was PCR amplified using primers 5'-CGCCTGGAGGACTTCAACTACAA-3' (SEQ ID NO:21) and 5'-TCCTCCCAATGTGGTAACCATCG-3' (SEQ ID NO:22) against GABA$_B$-R1b DNA as template. GABA$_B$-R2 cDNA probe, corresponding to residues 1397–1800, was amplified by PCR using primers 5'-ACAAGACCATCATCCTGGA-3' (SEQ ID NO:23) and 5'-GATCACAAGCAGTTTCTGGTC-3' (SEQ ID NO:24) with GABA$_B$-R2 DNA as template. DNA fragments were labelled with $^{32}$P-α-dCTP using a Rediprime DNA labelling system (Amersham). Probes were labelled to a specific activity of >10$^9$ cpm/μg and were used at a concentration of approximately 5 ng/ml hybridization solution. Following hybridization, blots were washed with 2×SSC/1% SDS at 65° C., and 0.1×SSC/0.5% SDS at 55° C. (20×SSC is 3M NaCl/0.3M Na$_3$Citrate.2H$_2$O pH7.0) and were exposed to X-ray film.

Yeast Two Hybrid Studies

Saccharomyces cerevisiae Y190 [MATa, gal4 gal80, ade2-101, his3, trp1-901, ura3-52, leu2-3,112, URA3::GAL1-lacZ, LYS2 ::GAL1-HIS3, cyh$^R$] was used for all described yeast two hybrid work (Harper et al., 1993, Clontech Laboratories, 1996). GAL4 binding-domain (GAL4$_{BD}$) fusion vectors were constructed in either pYTH9 (Fuller et al., 1998) or pYTH16, an episomal version of pYTH9. All GAL4 activation-domain fusions were made in pACT2 (Clontech Laboratories, 1998) All yeast manipulations were carried out using standard yeast media (Sherman, 1991). Human Brain MATCHMAKER library (HL4004AH) in pACT2 was purchased from Clontech Laboratories and amplified according to the manufacturers' instructions. The GABA$_B$-R1 C-terminal domain was amplified from a full length clone, using primers 5'-GTTGTCCCCATGGTGCCCAAGATGCGCA GGCTGATCACC-3' (SEQ ID NO:25) and 5'-GTCCTGCGGCCGCGGATCCTCACTTATAAAGCAA ATGCACT CG-3' (SEQ ID NO:26). PCR product was size-fractionated on 0.8% agarose gel, purified and force-cloned NcoI/NotI into pYTH9 and subsequently into pACT2. The GABA$_B$-R2 C-terminal domain was similarly generated with primers 5'-CTCTGCCCCATGGCCGTGCCGAAGCTCATCACCC TGA GAACAAACCC-3' (SEQ ID NO:27) and 5'-GGCCCAGGGCGGCCGCACTTACAGGCCCGAGAC CATGACTC GGAAGGAGGG-3' (SEQ ID NO:28) and subcloned into pYTH9, pYTH16 and pACT2. All cloned PCR products were sequenced and confirmed as error free.

The GAL4$_{BD}$-GABA$_B$-R1 C-terminus fusion in pYTH9 was stably integrated into the trp1 locus of Y190 by targetted homologous recombination. Yeast expressing GAL4$_{BD}$-GABA$_B$-R1 C-terminus were selected and transformed with Human brain cDNA library under leucine selection, using a high efficiency Lithium acetate transformation protocol (Clontech Laboratories, 1998). Sufficient independent cDNAs were transformed to give a three fold representation of the library. Interacting clones were selected by growth under 20 mM 3-amino-1,2,4-triazole (Sigma) selection, followed by production of β-galactosidase, as determined by a freeze-fracture assay (Clontech Laboratories, 1998). Plasmid DNA was recovered from yeast cells following digestion of the cell wall by 400 μg/ml Zymolase 100T (ICN Biochemicals) in 250 μl 1.2M Sorbitol; 0.1M potassium phosphate buffer (pH 7.4) at 37° or 2 h. Plasmid DNA was extracted by standard Qiagen alkaline lysis miniprep as per manufacturers' instructions and transformed into Ultracompetent XL-2Blue cells (Stratagene). Plasmid DNA was sequenced using primer 5'-CAGGGATGTTTAATACCACTACAATGG-3' (SEQ ID NO:29) using automated ABI sequencing and resulting sequences were blasted against the databases.

Yeast Y190 was transformed with pYTH16 and pACT2 expressing GABA$_B$-R1 C-terminal domain and the GABA$_B$-R2 C-terminal domain in all combinations, as well as against empty vectors. Transformants were grown in liquid media to mid-logarithmic phase and approximately 1.5 ml harvested. β-galactosidase activity was quantified using substrate o-nitrophenyl β-D-galactopyranoside (ONPG; Sigma) using a liquid nitrogen freeze fracture regime essentially as described by Harshman et al., (1988).

Two-microelectrode Voltage-clamp in Xenopus oocytes

Adult female Xenopus laevis (Blades Biologicals) were anaesthetised using 0.2% tricaine (3-aminobenzoic acid ethyl ester), killed and the ovaries rapidly removed. Oocytes were de-folliculated by collagenase digestion (Sigma type I, 1.5 mg ml$^{-1}$) in divalent cation-free OR2 solution (82.5 mM NaCl, 2.5 mM KCl, 1.2 mM NaH$_2$PO$_4$, 5 mM HEPES; pH 7.5 at 25° C.). Single stage V and VI oocytes were transferred to ND96 solution (96 mM NaCl, 2 mM KCl, 1 mM MgCl$_2$, 1.8 mM CaCl$_2$, 5 mM HEPES; pH 7.5 at 25° C.) which contained 50 μg ml$^{-1}$ gentamycin and stored at 18° C.

GABA$_B$-R1a, GABA$_B$-R1b (both in pcDNA3.1rev, Invitrogen), GABA$_B$-R2, GIRK1, GIRK4 (in pcDNA3) and cystic fibrosis transmembrane regulator (CFTR; in pBluescript, Stratagene) were linearised and transcribed to RNA using T7 or T3 polymerase (Promega Wizard kit). m'G(5')pp(5')GTP capped cRNA was injected into oocytes (20–50 nl of 1 μg$μ$l$^{-1}$ RNA per oocyte) and whole-cell currents were recorded using two-microelectrode voltage-clamp (Geneclamp amplifier, Axon instruments Inc.) 3 to 7 days post-RNA injection. Microelectrodes had a resistance of 0.5 to 2MΩ when filled with 3M KCl. In all experiments oocytes were voltage-clamped at a holding potential of −60 mV in ND96 solution (superfused at 2 ml per min.) and agonists were applied by addition to this extracellular solution. In GIRK experiments the extracellular solution was changed to a high potassium solution prior to agonist application, to facilitate the recording of inward potassium currents. Current-voltage curves were constructed by applying 200 ms voltage-clamp pulses from the holding potential of 60 mV to test potentials between −100 mV and +50 mV.

Mammalian Cell culture and transfections

HEK293T cells (HEK293 cells stably expressing the SV40 large T-antigen) were maintained in DMEM containing 10% (v/v) foetal calf serum and 2 mM glutamine. Cells were seeded in 60 mm culture dishes and grown to 60–80% confluency (18–24 h) prior to transfection with pCDNA3 containing the relevant DNA species using Lipofectamine reagent. For transfection, 3 μg of DNA was mixed with 10 μl of Lipofectamine in 0.2 ml of Opti-MEM (Life Technologies Inc.) and was incubated at room temperature for 30 min prior to the addition of 1.6 ml of Opti-MEM. Cells were exposed to the Lipofectamine/DNA mixture for 5 h and 2 ml of 20% (v/v) newborn calf serum in DMEM was then added. Cells were harvested 48–72 h after transfection.

Preparation of Membranes

Plasma membrane-containing P2 particulate fractions were prepared from cell pastes frozen at −80° C. after harvest. All procedures were carried out at 4° C. Cell pellets were resuspended in 1 ml of 10 mM Tris-HCl and 0.1 mM EDTA, pH 7.5 (buffer A) and by homogenisation for 20 s with a polytron homogeniser followed by passage (5 times) through a 25-guage needle. Cell lysates were centrifuged at 1,000 g for 10 min in a microcentrifuge to pellet the nuclei and unbroken cells and P2 particulate fractions were recovered by microcentrifugation at 16,000 g for 30 min. P2 particulate fractions were resuspended in buffer A and stored at −80° C. until required. Protein concentrations were determined using the bicinchoninic acid (BCA) procedure (Smith et al., 1985) using BSA as a standard.

High Affinity [$^{35}$S]GTPγS Binding

Assays were performed in 96-well format using a method modified from Wieland and Jakobs, 1994. Membranes (10 mg per point) were diluted to 0.083 mg/ml in assay buffer (20 mM HEPES, 100 mM NaCl, 10 mM MgCl$_2$, pH7.4) supplemented with saponin (10 mg/l) and pre-incubated with 40 mM GDP. Various concentrations of GABA were added, followed by [$^{35}$S]GTPgS (1170 Ci/mmol, Amersham) at 0.3 nM (total vol. of 100 ml) and binding was allowed to proceed at room temperature for 30 min. Non-specific binding was determined by the inclusion of 0.6 mM GTP. Wheatgerm agglutinin SPA beads (Amersham) (0.5 mg) in 25 ml assay buffer were added and the whole was incubated at room temperature for 30 min with agitation. Plates were centrifuged at 1500 g for 5 min and bound [$^{35}$S]GTPgS was determined by scintillation counting on a Wallac 1450 microbeta Trilux scintillation counter.

Measurement of cAMP Levels 24 hours following transfection, each 60 mm dish of HEK293T cells was split into 36 wells of a 96-well plate and the cells were allowed to reattach overnight. Cells were washed with PBS and pre-incubated in DMEM medium containing 300 μM IBMX for 30 minutes at 37° C. Forskolin (50 μM) and varying concentrations of GABA were added and cells incubated for a further 30 min prior to cAMP extraction with 0.1M HCl for 1 h at 4° C. Assays were neutralised with 0.1 M KHCO$_3$ and cAMP levels determined using scintillation proximity assays (Biotrak Kit, Amersham).

Flow Cytometric Analysis

HEK293T cells were transiently transfected with cDNA as described. 48–72 h following transfection, cells were recovered and washed twice in PBS supplemented with 0.1% (w/v) NaN$_3$ and 2.5% (v/v) foetal calf serum. Cells were resuspended in buffer and incubated with primary antibodies 9E10 (c-Myc) or 12CA5 (HA) for 15 min at room temperature. Following three further washes with PBS, cells were incubated with secondary antibody (sheep anti-mouse Fab$_2$ coupled with fluorescein isothiocyanate (FITC)) diluted 1:30 for 15 min at room temperature. For permeabilised cells, a Fix and Perm kit (Caltag) was used. Cell analysis was performed on a Coulter Elite flow-cytometer set up to detect FITC fluoresence. 30,000 cells were analysed for each sample.

Immunological Studies

Antiserum 501 was raised against a synthetic peptide corresponding to the C-terminal 15 amino acids of the GABA$_B$-R1 receptor and was produced in a sheep, using a conjugate of this peptide and keyhole limpet hemocyanin (Calbiochem) as antigen. Membrane samples 30–60 μg) were resolved by SDS-PAGE using 10% (w/v) acrylamide. Following electrophoresis, proteins were subsequently transferred to nitrocellulose (Hybond ECL, Amersham), probed with antiserum 501 at 1:1000 dilution and visualised by enhanced chemiluminescence (ECL, Amersham).

Epitope tags were visualised by immunoblotting with anti-Myc (9E10; 1:100 dilution) or anti-HA (12CA5; 1:500) monoclonal antibodies.

Deglycosylation

Enzymatic removal of asparagine-linked (N-linked) carbohydrate moieties with endoglycosidases F and H was performed essentially according to manufacturers' instructions (Boehringer Mannheim) using 50 μg of membrane protein per enzyme reaction. GABA$_B$ receptor glycosylation status was studied following SDS-PAGE/immunoblotting of samples.

Immunoprecipitation Procedures

Transiently transfected HEK293T cells were harvested as described above from 60 mm culture dishes. Cells from each dish were resuspended in 1 ml of 50 mM Tris-HCl, 150 mM NaCl, 1% (v/v) Nonidet® P40, 0.5% (w/v) sodium deoxycholate, pH 7.5 (lysis buffer) supplemented with Completes protease inhibitor cocktail tablets (1 tablet/25 ml) (Boehringer Mannheim). Cell lysis and membrane protein solubilisation was achieved by homogenisation for 20 seconds with a polytron homogeniser, followed by gentle mixing for 30 min at 4° C. Insoluble debris was removed by microcentrifugation at 16,000 g for 15 min at 4° C. and the supernatant was pre-cleared by incubating with 50 μl of Protein A-agarose (Boehringer Mannheim) for 3 h at 4° C. on a helical wheel to reduce non-specific background. Solubilised supernatant was divided into 2×500 μl aliquots and 20 μl of either HA or Myc antisera was added to each. Immunoprecipitation was allowed to proceed for 1 h at 4° C. on a helical wheel prior to the addition of 50 μl of Protein A-agarose suspension. Capture of immune complexes was progressed overnight at 4° C. on a helical wheel. Complexes were collected by microcentrifugation 12,000 g for 1 min at 4° C. and supernatant was discarded. Beads were washed by gentle resuspension and agitation sequentially in 1 ml of 50 mM Tris-HCl, pH 7.5, 500 mM NaCl, 0.1% (v/v) Nonidet® P40 and 0.05% (w/v) sodium deoxycholate followed by 1 ml of 50 mM Tris-HCl, pH 7.5, 0.1% (v/v) Nonidet® P40 and 0.05% (w/v) sodium deoxycholate. Immunoprecipitated proteins were released from Protein A-agarose by incubation in 30 μl of SDS-PAGE sample buffer at 70° C. for 10 min and analysed by SDS-PAGE followed by immunoblotting.

Binding Assays

Competition binding assays were performed in 50 mM Tris HCl buffer (pH7.4) containing 40 μM isoguvacine (Tocris Cookson) to block rat brain GABA$_A$ binding sites. P2 membrane preparations were made from HEK293T cells transfected using conditions described above. Increasing concentrations of GABA were added to displace the antagonist [3H]-CGP 54626 (Tocris Cookson, 40 Ci/mmol). Assay conditions were 0.4–0.6 nM [$^3$H]-CGP54626, incubated with 50 μg/tube crude rat brain 'mitochondrial' fractions or 25 μg/tube HEK293T P2 membranes at room temperature for 20 minutes. The total volume per tube was 0.5 ml and non specific binding was determined using 1 mM GABA. Bound ligand was recovered using a Brandel 48 well harvester onto GF/B filters (Whatman) and measured by liquid scintillation using a Beckman LS6500 counter.

REFERENCES

Bettler, B., Kaupmann, K and Bowery, N. Curr Opin in Neurobiol 8: 345–350 (1998)

Bittiger, H., Froestl, W., Gentsch, C., Jaekel., J., Mickel, S. J., Mondori, C., Olpe, H. R., Schmuz, M. (1996) in GABA: receptors, transporters and metabolism Ed: C. Tanaka and N. G. Bowery. Birkhauser Verlag Basel Switzerland.

Bittiger, H., Reymann, N., Froestl, W. & Mickel, S. J. *Pharmacology Communications* 2:1–2: 23 (1992)

Bowery, N. G., Hudson, A. L., Price, G. W. *Neuroscience* 20: 365–383 (1987)

Chou, K. C. and Heinrikson, R. L. *J. Protein Chem* 16: 765–773 (1997)

Clontech Laboratories. CLONTECH MATCHMAKER™ GAL4 Two Hybrid system User Manual, Protocol PT3061-1. Palo Alto, Calif. (1996)

Cvejic, S. and Devi, L. A. *J. Biol Chem* 272: 26959–26964 (1997)

Fuller, K. J., Morse, M. A., White, J. H. M., Dowell, S. J. and Sims, M. J. *BioTechniques* 25: 85–92 (1998)

Gemignani, A., Paudice, P., Bonanno, G., Raiteri, M. *Mol Pharmacol* 46: 558–562 (1994)

Harayama, N., Shibuya, I., Tanaka, K., Kabashima, N., Ueta, Y., Yamashita, H. *J. Physiol (Lond)* 509: 371–383 (1998)

Harper, J. W., Adami, G. R., Wei, N. Keyomarsi, K. and Elledge, S. J. *Cell* 75: 805–816 (1993)

Harshmann, K. D., Moye-Rowley, W. S. and Parker, C. S. *Cell* 53: 321–330 (1988)

Hebert, T. E. and Bouvier, M. *Biochem. Cell. Biol.* 76: 1–11 (1998)

Hebert, T. E., Moffett, S., Morello, J. P., Loisel, T. P., Bichet, D. G., Barret, C., and Bouvier, M. *J. Biol Chem* 271: 16384–16392 (1997)

Hill, D. R. and Bowery, N. G. *Nature (Lond)* 290: 149–152 (1981)

Kaprivinsky, G., Gordon, E. A., Wickman, K., Velimirovic, B., Kaprivinsky, L. and Clapham, D. E. *Nature (Lond)* 374:135–141 (1995)

Kaupmann, K., Huggel, K., Heid, J., Flor, P. J., Bischoff, S., Mickel., S. J., McMaster, G., Angst, C., Bittiger, H., Froestl, W. and Bettler, B. *Nature(Lond)* 386, 239–246 (1997)

Kerr, D. I., Humeniuk, R. E., and Ong, J. *Eur. J. Pharmacol.* 262: 189–192 (1994)

Kerr, D. I. and Ong, J. *Pharmacol. Ther.* 67: 187–246 (1995)

Kerr, D. I. and Ong, J. *DDT* 1: 371–380 (1996)

Kobrinsky, E. M., Pearson, H. A. and Dolphin, A. C. *Neuroscience* 58: 539–552 (1994).

Kovoor, A., Nappey, V., Kieffer, B. L. and Chavkin, C. *J. Biol. Chem.* 272: 27605–27611. (1997)

Kubo, Y., Reuveny, E., Slesinger, P. A., Jan, Y. H. and Jan, L. Y. *Nature (Lond)* 364: 802–806. (1993)

Lovinger, D. M., Harrison, N. L. and Lambert, N. A. *Eur. J. Pharmacol.* 211: 337–341(1992)

Lupas, A. *Trends in Biol. Sci.* 21: 375–382 (1996)

Malcangio, M. and Bowery, N. G. *Clin Neuropharmacol* 18: 285–305 (1995)

McLatchie, L. M., Fraser N. J., Main, M. J. Wise A., Brown, J., Thompson, N., Solari, R., Lee, M. G and Foord, S. M. *Nature (Lond)* 393: 333–339 (1998)

Menon-Johansson, A. S., Berrow, N. and Dolphin, A. C. *Pflugers Arch* 425: 335–343 (1993)

Ohmori, Y., Hirouchi, M., Taguchim J. and Kuriyama, K. *J. Neurochem* 54: 80–85 (1990)

Ong, J., Kerr, D. I., Doolette, D. J., Duke, R. K., Mewett, K. N., Allen, R. D. and Johnston, G. A. *Eur J Pharmacol* 233:169–172 (1993).

O'Hara, P. J., Sheppard, P. O., Thogersen, H., Venezia, D., Haldeman, B. A., McGrane, V., Houamed, K. M., Thomsen, C., Gilbert, T. L. and Mulvihill, E. R. *Neuron* 11: 41–52 (1993)

Raiteri, M., Bonanno, G., Gemignani, A., Pende, M., Vellebuona, F. and Lanza, M. *Adv. Biochem. Psychopharmacol.* 47: 205–216 (1992)

Romano, C., Yang, W-L. and O'Malley, K. L. *J. Biol.Chem.* 271: 28612–28616 (1996).

Sambrook, J., Fritsch, E. F. and Maniatis, T. Molecular Cloning: a Laboratory Manual. $2^{nd}$ Edition. CSH Laboratory Press. (1989)

Sherman, F. *Methods Enzymol.* 194: 3–21 (1991)

Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D. C. *Anal. Biochem.* 150: 76–85 (1985)

Takahashi, K, Tsuchida, K., Tanabe, Y., Masu, M. and Nakanishi, S. *J. Biol. Chem.* 268: 19341–19345 (1993)

Uezono, Y., Bradley, J., Min, C., McCarty, N. A., Quick, M., Riordan, J. R., Chavkin, C., Zinn, K., Lester, A. and Davidson, N. *Receptors and Channels* 1: 233–241 (1993)

Wotta, D. R., Bimbaum, A. K., Wilcox, G. L., Elde, R. and Law, P. Y. *Brain Res. Mol. Brain Res.* 44: 5565 (1997)

---

I claim:

1. An isolated GABA$_B$-R2 receptor protein having an amino acid sequence set forth in SEQ ID NO:31.

2. An isolated human GABA$_B$-R2 receptor protein having an amino acid sequence encoded by the nucleic acid sequence set forth in SEQ ID NO:30.

3. An isolated human GABA$_B$-R2 receptor protein having the amino acid sequence set forth in SEQ ID NO:31.

* * * * *

UNITED STATES PATENT AND TRADEMARK OFFICE
CERTIFICATE OF CORRECTION

PATENT NO.    : 6,518,399 B1
DATED         : February 11, 2003
INVENTOR(S)   : Marshall et al.

It is certified that error appears in the above-identified patent and that said Letters Patent is hereby corrected as shown below:

Title page,
Item [75], Inventors, reads "Ashley Antony Barnes, Herts (GB); Alan Wise, Bedfordshire (GB); Fiona Hamilton Marshall, Hertfordshire (GB); Neil James Fraser, Herts (GB); Julia Helen Margaret White ; Herts (GB); Steven Micheal Foord, Buckinghamshire (GB)" should read -- Fiona Hamilton Marshall, Hertfordshire (GB); Neil James Fraser, Herts (GB); Steven Micheal Foord, Buckinghamshire (GB) --

Signed and Sealed this

Seventeenth Day of August, 2004

JON W. DUDAS
*Acting Director of the United States Patent and Trademark Office*